United States Patent
Bar et al.

(10) Patent No.: US 11,058,411 B2
(45) Date of Patent: Jul. 13, 2021

(54) ANCHORS AND LOCKS FOR PERCUTANEOUS VALVE IMPLANTS

(71) Applicant: VALFIX MEDICAL LTD., Tel Aviv (IL)

(72) Inventors: Eli Bar, Megadim (IL); Elad Yaacoby, Kfar Shmuel (IL); Dan Salzman, Jerusalem (IL)

(73) Assignee: VALFIX MEDICAL LTD., Tel Aviv (IL)

( * ) Notice: Subject to any disclaimer, the term of this patent is extended or adjusted under 35 U.S.C. 154(b) by 0 days.

(21) Appl. No.: 16/962,233

(22) PCT Filed: Jan. 13, 2020

(86) PCT No.: PCT/IB2020/050228
§ 371 (c)(1),
(2) Date: Jul. 15, 2020

(87) PCT Pub. No.: WO2020/148629
PCT Pub. Date: Jul. 23, 2020

(65) Prior Publication Data
US 2021/0015476 A1 Jan. 21, 2021

Related U.S. Application Data

(60) Provisional application No. 62/791,912, filed on Jan. 14, 2019.

(51) Int. Cl.
*A61B 17/04* (2006.01)
*A61F 2/24* (2006.01)

(52) U.S. Cl.
CPC ........ *A61B 17/0401* (2013.01); *A61F 2/2427* (2013.01); *A61B 2017/0409* (2013.01);
(Continued)

(58) Field of Classification Search
CPC .. A61F 2/2442; A61F 2/2427; A61B 17/0401; A61B 2017/0409;
(Continued)

(56) References Cited

U.S. PATENT DOCUMENTS 6,786,925 B1 9/2004 Schoon et al.
7,678,123 B2 * 3/2010 Chanduszko ...... A61B 17/0057
606/151

(Continued)

FOREIGN PATENT DOCUMENTS

EP 1549394 A2 7/2005
EP 2793763 A1 10/2014
EP 3345572 A1 7/2018

OTHER PUBLICATIONS

European application # 18748693.1 search report dated Jul. 16, 2020.
(Continued)

*Primary Examiner* — Phong Son H Dang
(74) *Attorney, Agent, or Firm* — Kligler & Associates Patent Attorneys Ltd

(57) ABSTRACT

An apparatus includes a thread (58) and a tissue anchor (60) coupled to the thread. The anchor includes a proximal portion (60*p*), shaped to define one or more appendages (82), a distal portion (60*d*), and a plurality of strips (84) joining the proximal portion to the distal portion. The anchor is configured to anchor the thread at tissue (42) of a subject by virtue of the appendages expanding radially, and the strips expanding radially to form respective loops at a distal side of the tissue, upon removal of a radially-constraining force from the anchor. Other embodiments are also described.

19 Claims, 19 Drawing Sheets

(52) U.S. Cl.
CPC ............... *A61B 2017/0412* (2013.01); *A61B 2017/0414* (2013.01); *A61B 2017/0464* (2013.01); *A61B 2017/0477* (2013.01); *A61F 2220/0016* (2013.01)

(58) Field of Classification Search
CPC .... A61B 2017/0414; A61B 2017/0464; A61B 2017/0477
See application file for complete search history.

(56) References Cited

U.S. PATENT DOCUMENTS

| | | | |
|---|---|---|---|
| 7,722,666 B2 | 5/2010 | Lafontaine | |
| 7,988,725 B2 | 2/2011 | Gross et al. | |
| 8,216,302 B2* | 7/2012 | Wilson | A61F 2/246 623/2.11 |
| 8,328,868 B2 | 12/2012 | Paul et al. | |
| 8,449,606 B2* | 5/2013 | Eliasen | A61F 2/246 623/2.11 |
| 9,078,645 B2 | 7/2015 | Conklin et al. | |
| 9,089,313 B2 | 7/2015 | Roue et al. | |
| 9,132,009 B2 | 9/2015 | Hacohen et al. | |
| 9,149,358 B2 | 10/2015 | Tabor et al. | |
| 9,180,005 B1 | 11/2015 | Lashinski et al. | |
| 9,241,702 B2 | 1/2016 | Maisano et al. | |
| 9,308,066 B2* | 4/2016 | Molgaard-Nielsen | A61F 2/00 |
| 9,675,454 B2* | 6/2017 | Vidlund | A61F 2/2439 |
| 9,693,780 B2 | 7/2017 | Miles et al. | |
| 9,750,607 B2 | 9/2017 | Ganesan et al. | |
| 9,925,079 B2 | 3/2018 | Tabor et al. | |
| 10,111,686 B2* | 10/2018 | Bartosch | A61B 17/3468 |
| 10,278,820 B2 | 5/2019 | Bar et al. | |
| 10,335,275 B2 | 7/2019 | Lashinski et al. | |
| 10,376,361 B2 | 8/2019 | Gross et al. | |
| 10,463,486 B2 | 11/2019 | Bar et al. | |
| 2004/0034380 A1 | 2/2004 | Woolfson et al. | |
| 2006/0135967 A1 | 6/2006 | Realyvasquez | |
| 2007/0016288 A1 | 1/2007 | Gurskis et al. | |
| 2007/0032820 A1* | 2/2007 | Chin-Chen | A61B 17/0057 606/213 |
| 2007/0073337 A1* | 3/2007 | Abbott | A61B 17/12122 606/213 |
| 2007/0093890 A1* | 4/2007 | Eliasen | A61F 2/246 623/2.11 |
| 2007/0106328 A1 | 5/2007 | Wardle et al. | |
| 2007/0167981 A1* | 7/2007 | Opolski | A61B 17/0057 606/213 |
| 2007/0265700 A1* | 11/2007 | Eliasen | A61F 2/246 623/2.1 |
| 2007/0270943 A1* | 11/2007 | Solem | A61F 2/246 623/2.11 |
| 2008/0015635 A1* | 1/2008 | Olsen | A61B 17/0057 606/213 |
| 2008/0306586 A1 | 12/2008 | Cartledge et al. | |
| 2009/0048668 A1* | 2/2009 | Wilson | A61F 2/2466 623/2.36 |
| 2009/0131849 A1* | 5/2009 | Maurer | A61F 2/246 604/9 |
| 2010/0063542 A1* | 3/2010 | van der Burg | A61B 17/0401 606/232 |
| 2010/0161047 A1* | 6/2010 | Cabiri | A61B 17/072 623/2.37 |
| 2010/0179648 A1 | 7/2010 | Richter et al. | |
| 2010/0198258 A1* | 8/2010 | Heaven | A61B 17/0401 606/232 |
| 2010/0280604 A1* | 11/2010 | Zipory | A61B 17/0401 623/2.11 |
| 2011/0166649 A1 | 7/2011 | Gross et al. | |
| 2012/0059458 A1 | 3/2012 | Buchbinder et al. | |
| 2012/0123531 A1 | 5/2012 | Tsukashima et al. | |
| 2012/0245604 A1 | 9/2012 | Tegzes | |
| 2012/0283757 A1 | 11/2012 | Miller et al. | |
| 2012/0296160 A1* | 11/2012 | Hill | A61F 2/2466 600/104 |
| 2013/0123910 A1 | 5/2013 | Cartledge et al. | |
| 2013/0172978 A1* | 7/2013 | Vidlund | A61F 2/2439 623/1.12 |
| 2013/0226289 A1 | 8/2013 | Shaolian et al. | |
| 2013/0304197 A1 | 11/2013 | Buchbinder et al. | |
| 2013/0324907 A1* | 12/2013 | Huntley | A61B 17/068 604/8 |
| 2013/0331930 A1 | 12/2013 | Rowe et al. | |
| 2014/0031930 A1 | 1/2014 | Keidar et al. | |
| 2014/0172076 A1* | 6/2014 | Jonsson | A61F 2/2445 623/2.11 |
| 2014/0309730 A1 | 10/2014 | Alon et al. | |
| 2014/0343602 A1* | 11/2014 | Cox | A61B 17/12113 606/215 |
| 2015/0005810 A1* | 1/2015 | Center | A61F 2/01 606/200 |
| 2015/0142101 A1* | 5/2015 | Coleman | A61B 17/0057 623/2.11 |
| 2015/0157268 A1* | 6/2015 | Winshtein | A61B 5/6882 600/508 |
| 2015/0173897 A1 | 6/2015 | Raanani et al. | |
| 2015/0223934 A1* | 8/2015 | Vidlund | A61F 2/2412 623/2.11 |
| 2015/0245910 A1 | 9/2015 | Righini et al. | |
| 2015/0366556 A1* | 12/2015 | Khairkhahan | A61B 17/0401 606/232 |
| 2016/0015515 A1 | 1/2016 | Lashinski et al. | |
| 2017/0258585 A1 | 9/2017 | Marquez et al. | |
| 2018/0369594 A1* | 12/2018 | Werneth | A61B 17/0057 |
| 2019/0000613 A1* | 1/2019 | Delgado | A61B 17/3468 |
| 2019/0183512 A1* | 6/2019 | Subramaniam | A61B 17/12145 |
| 2019/0269511 A1 | 9/2019 | Bar et al. | |
| 2020/0015971 A1* | 1/2020 | Brauon | A61B 17/0487 |

OTHER PUBLICATIONS

International Application # PCT/IB2020/050226 search report dated May 27, 2020.
International Application # PCT/IB2020/050228 search report dated Apr. 21, 2020.
International Application # PCT/IB2020/050226 filed Jan. 13, 2020.

* cited by examiner

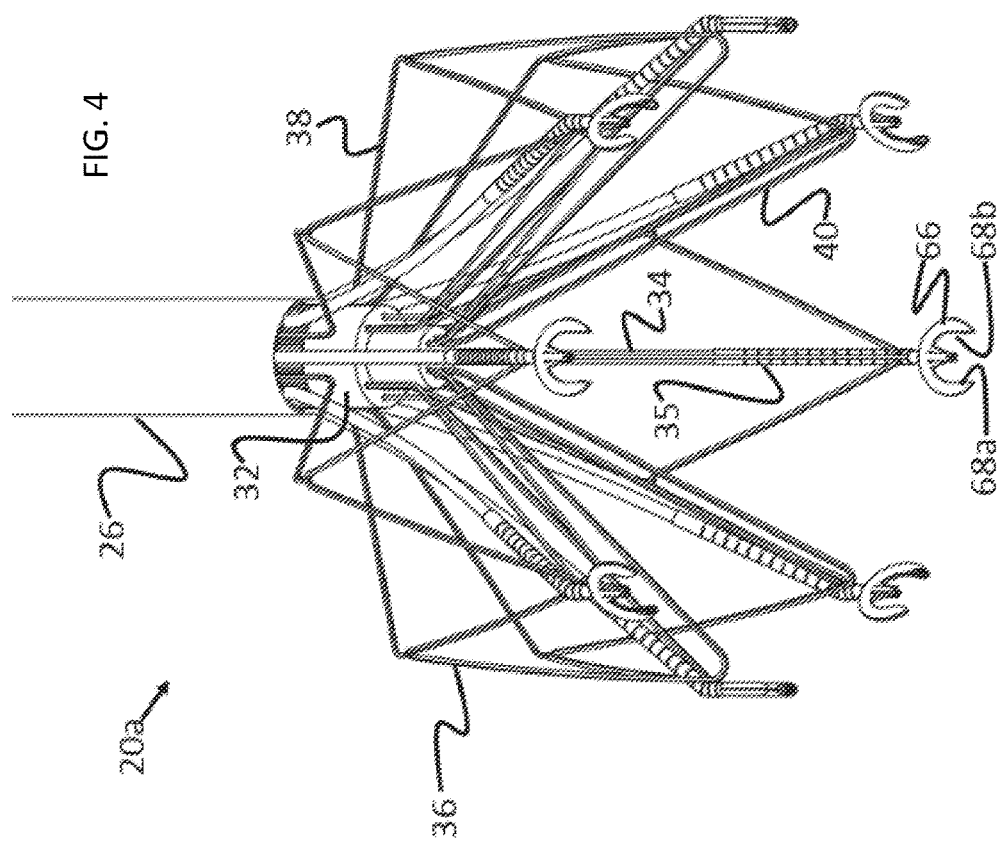
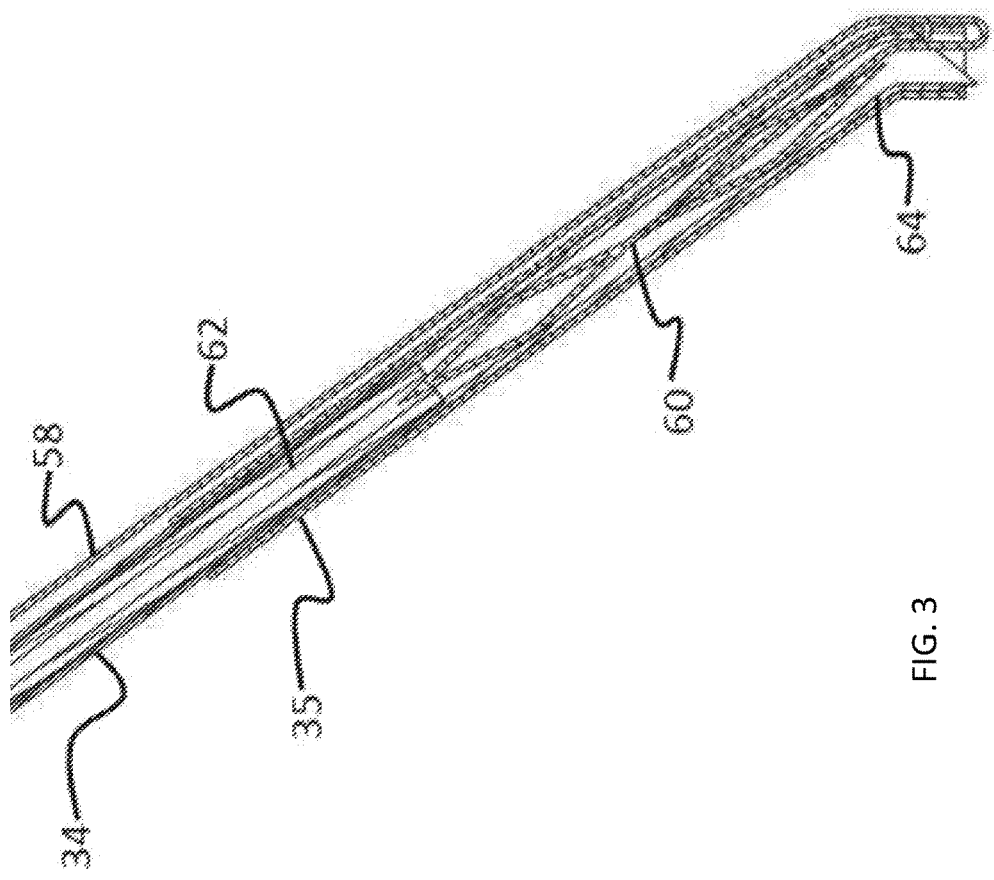

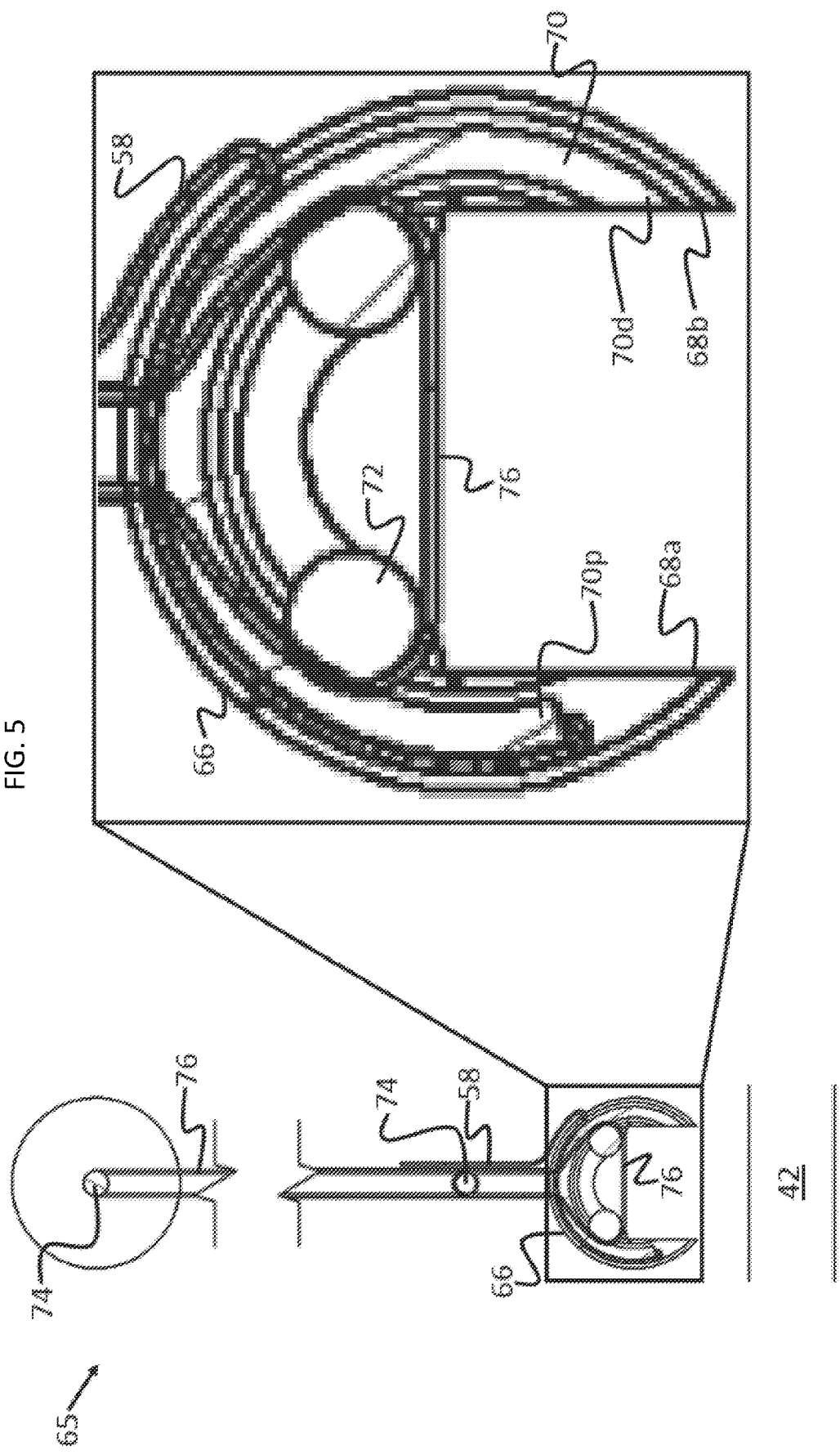

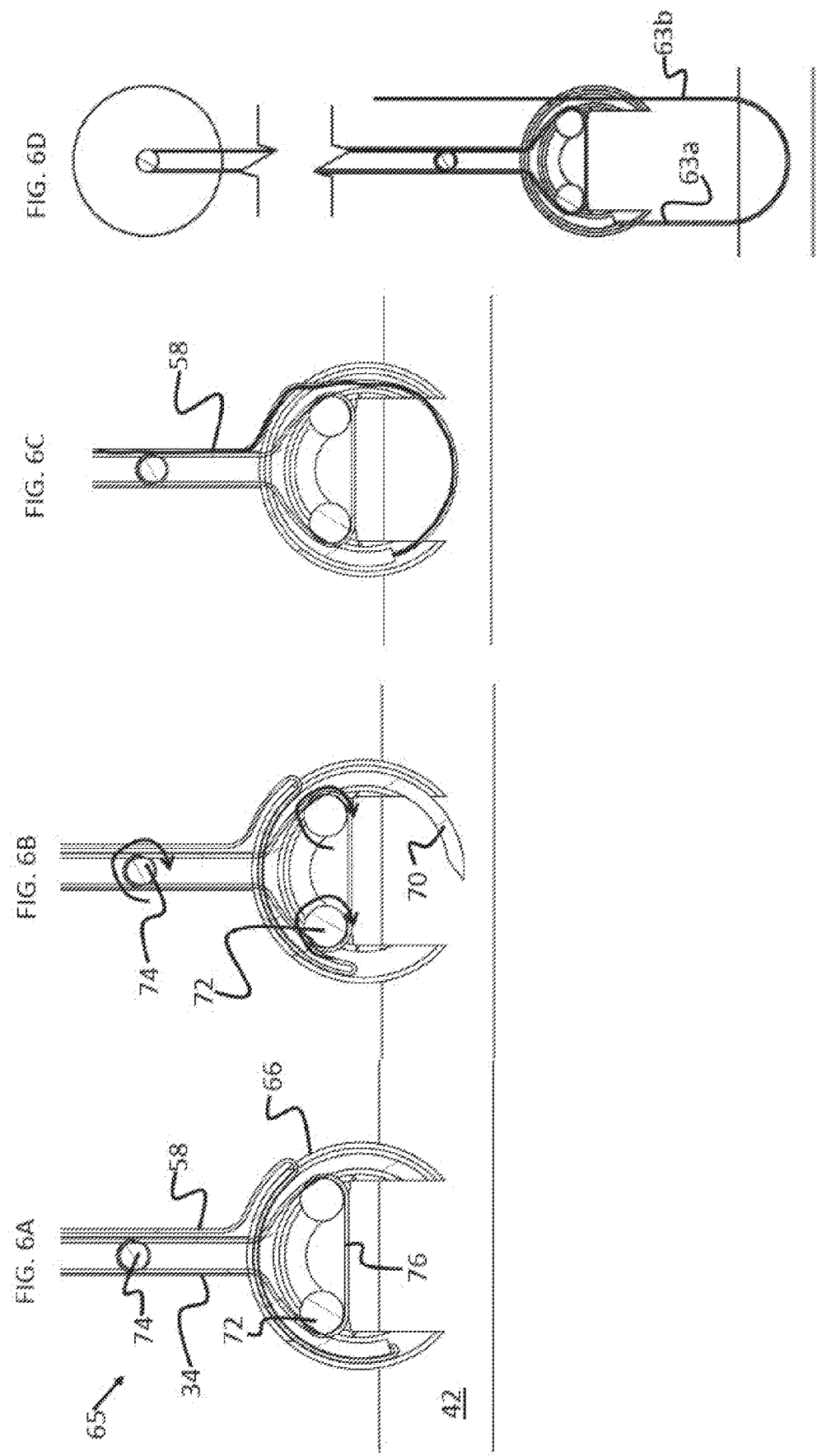

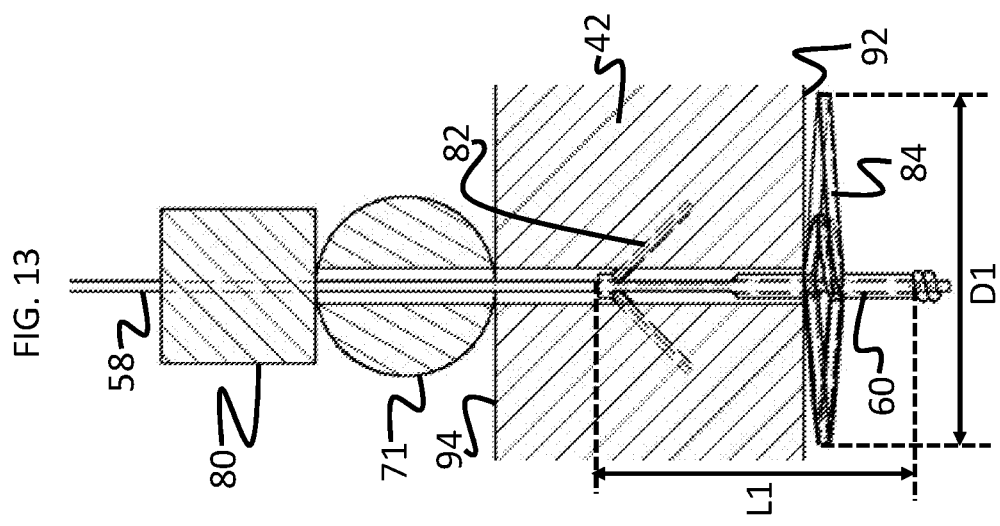
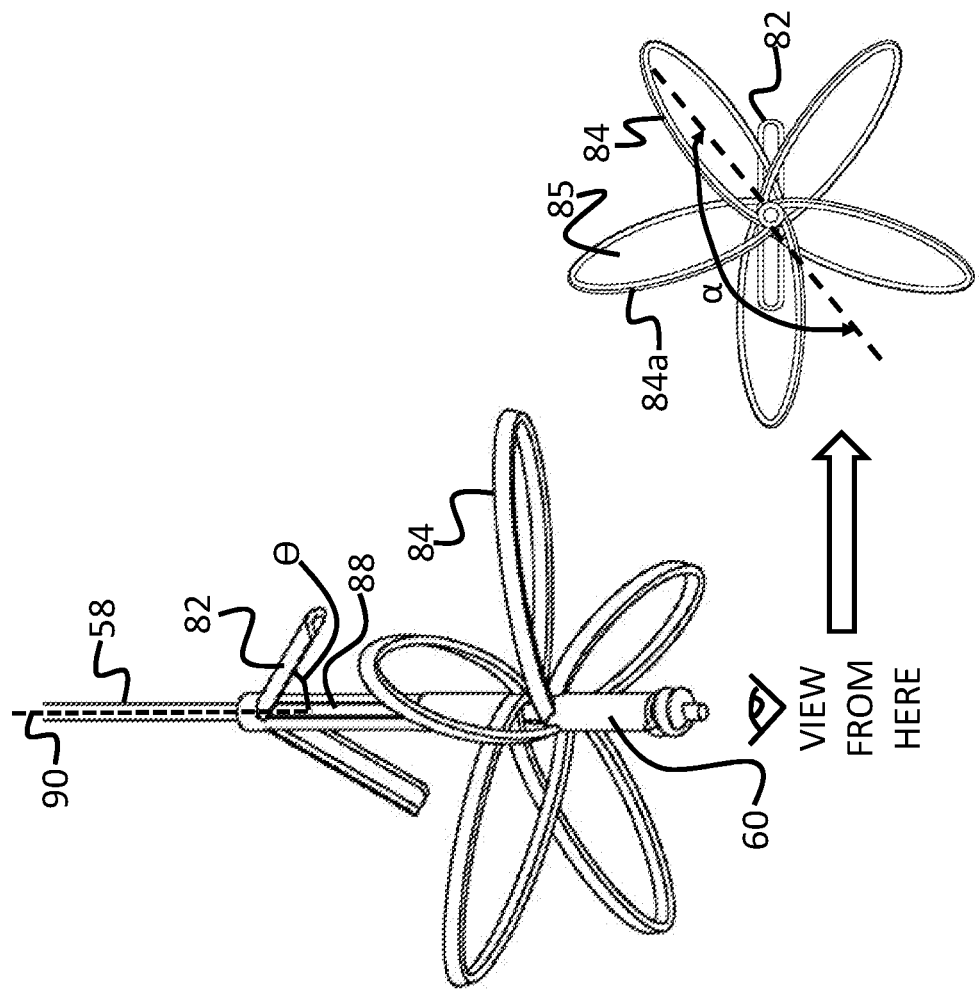

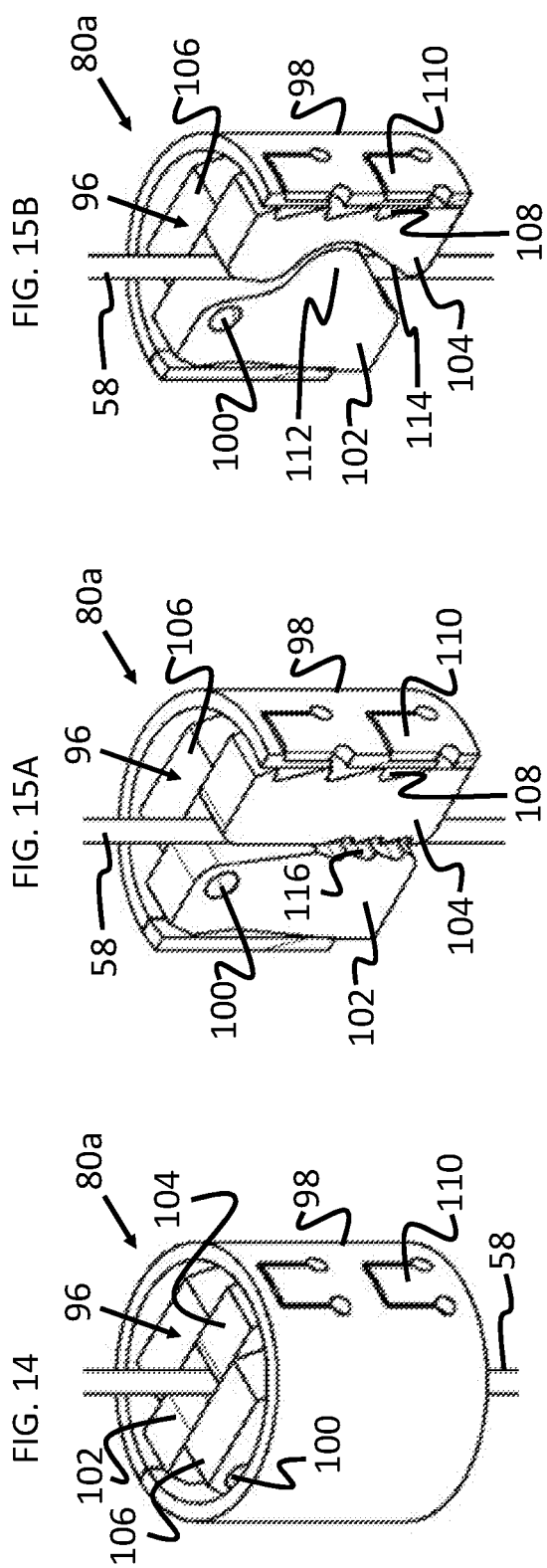

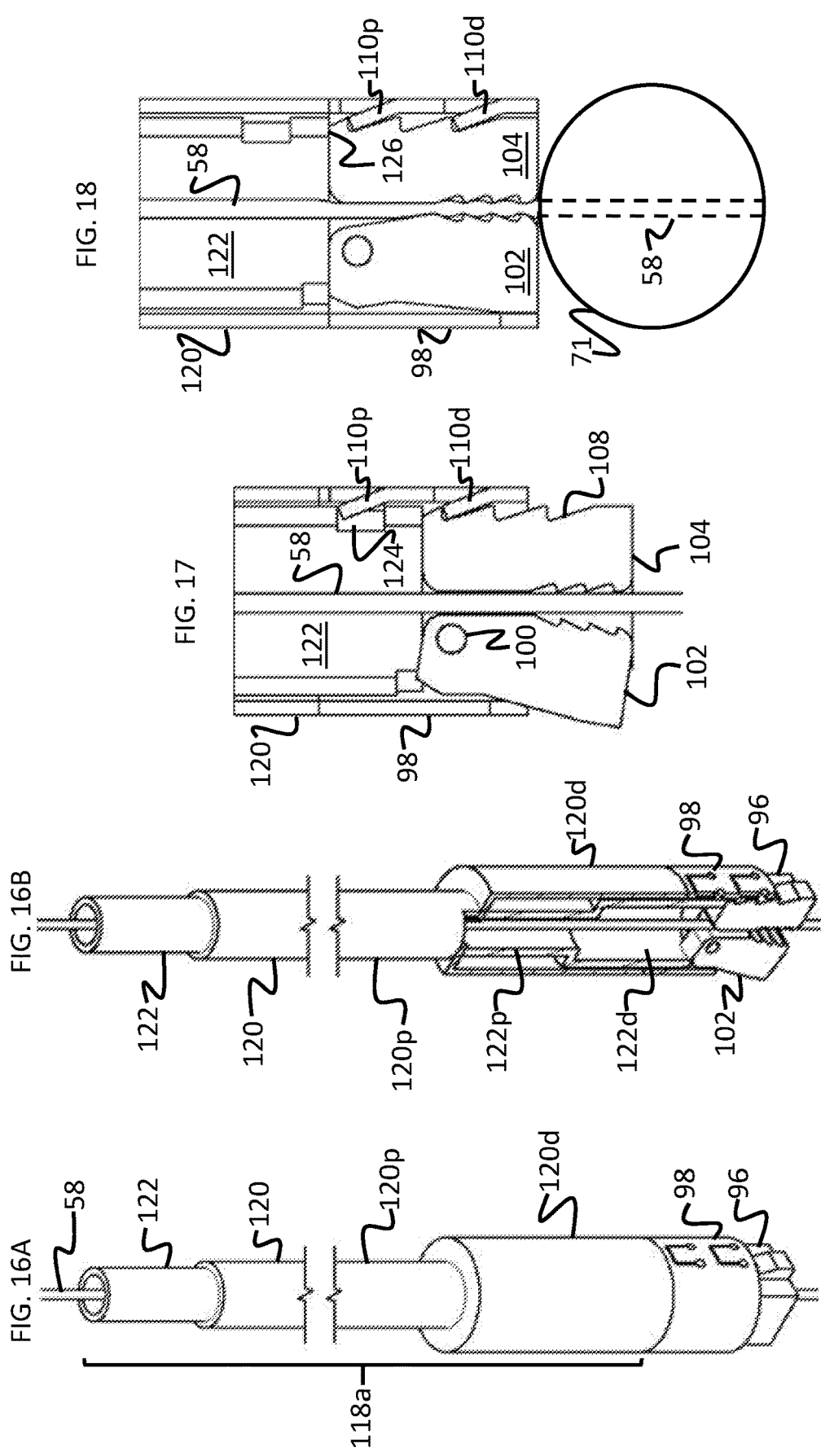

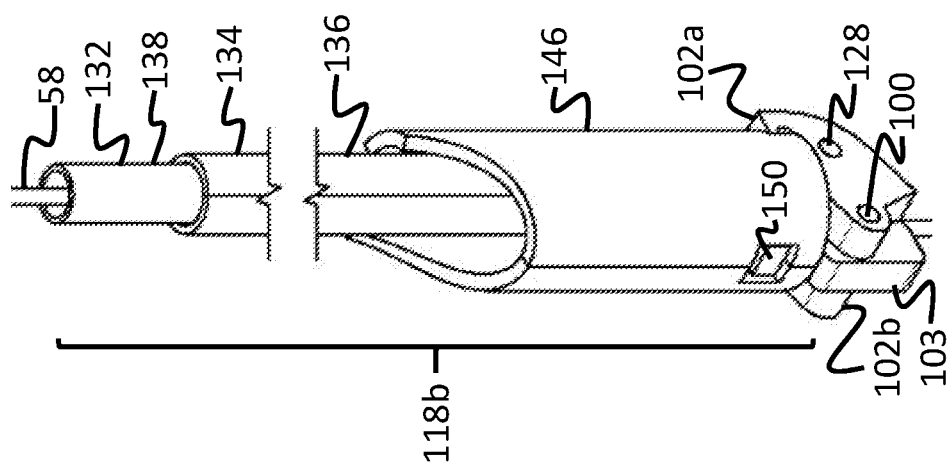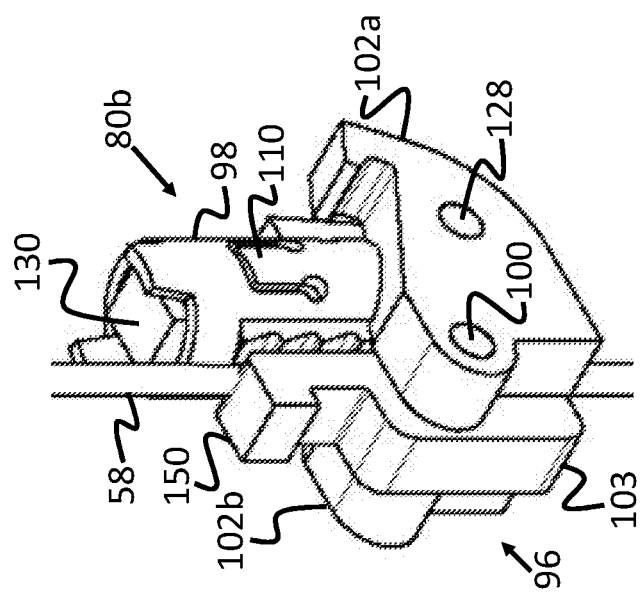

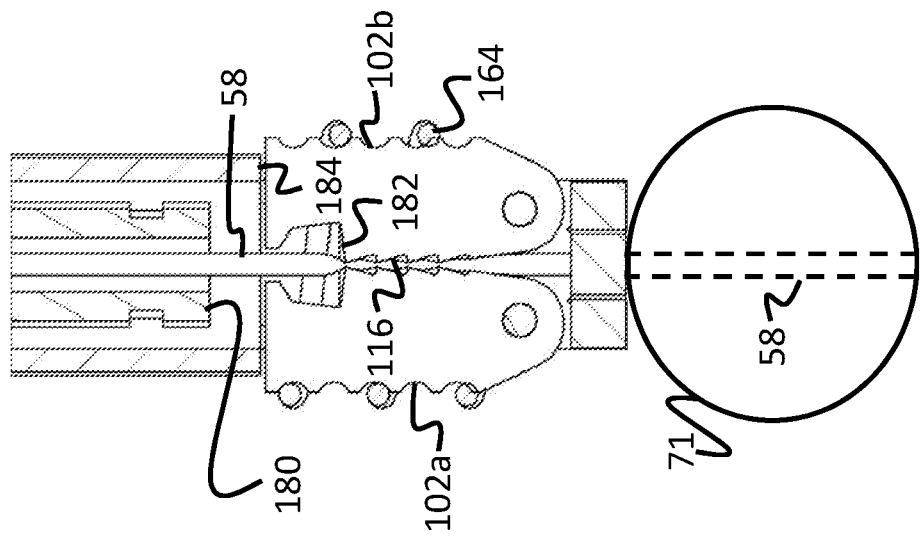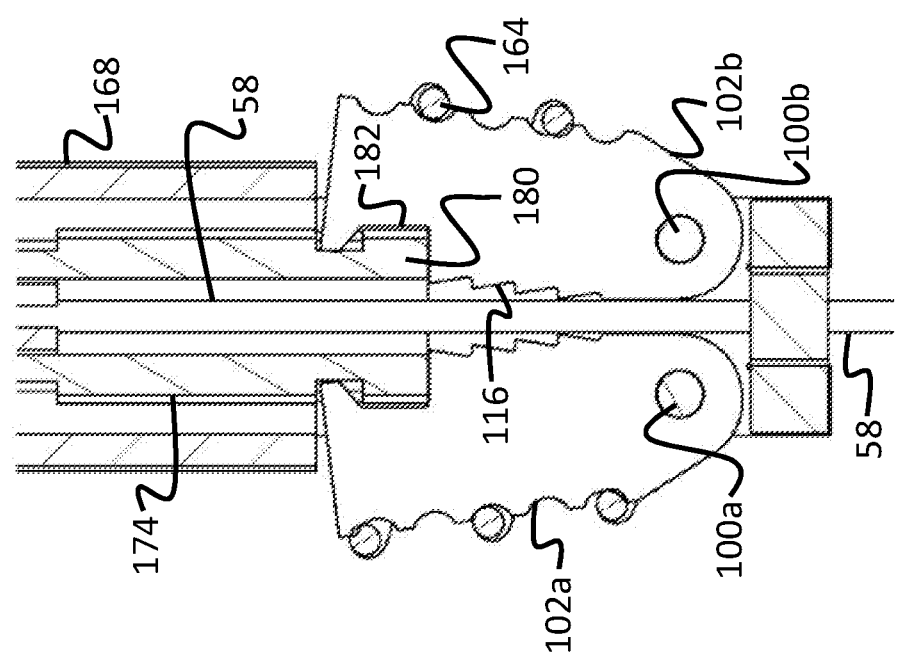

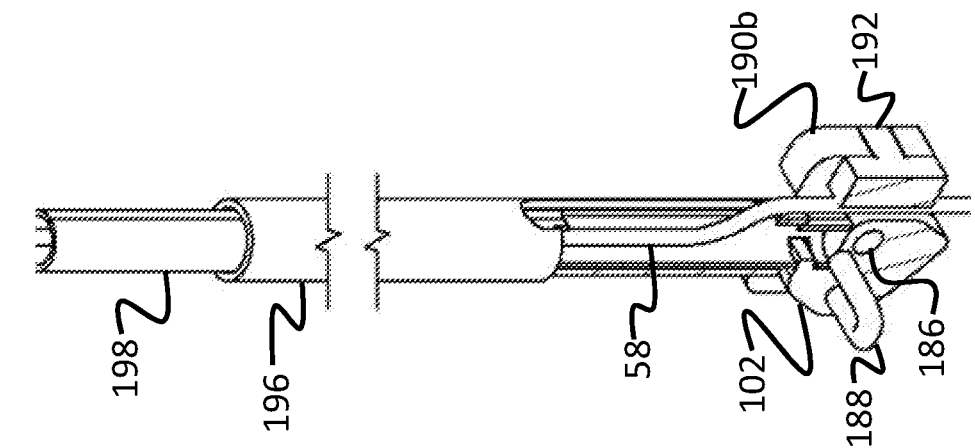
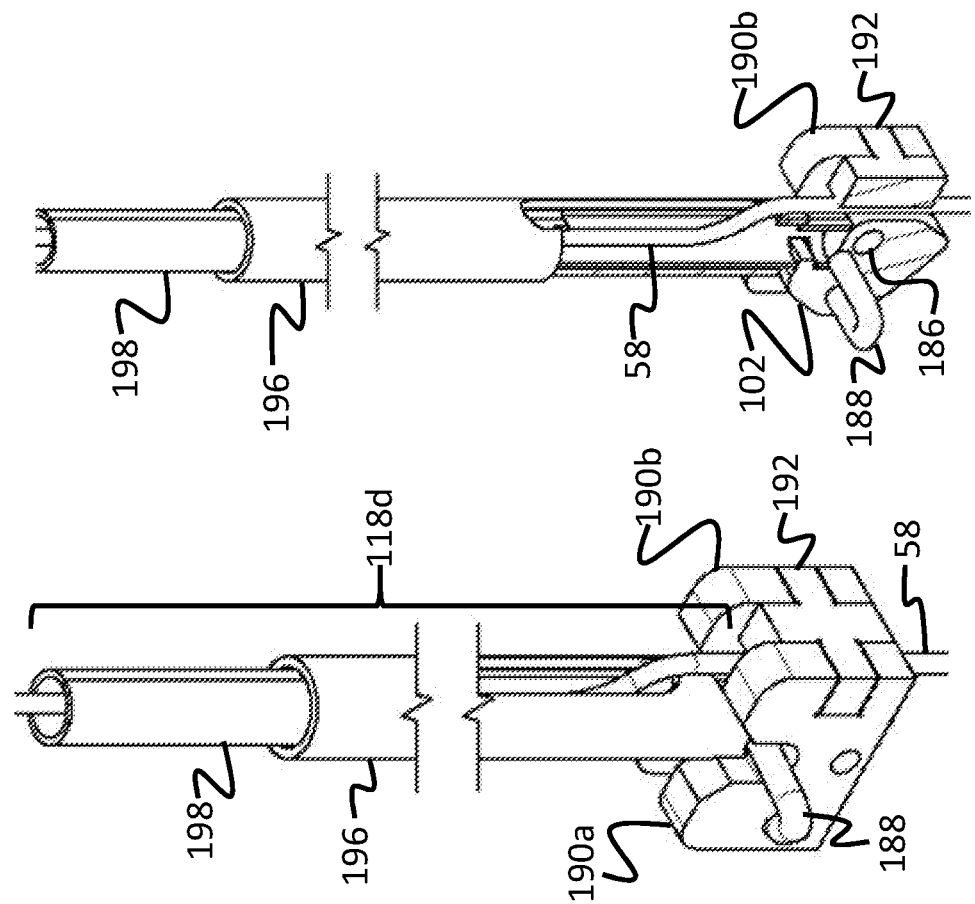
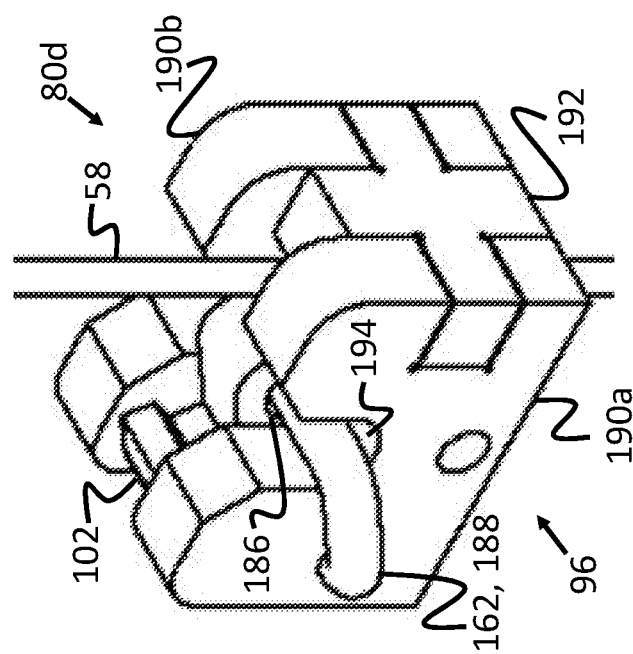

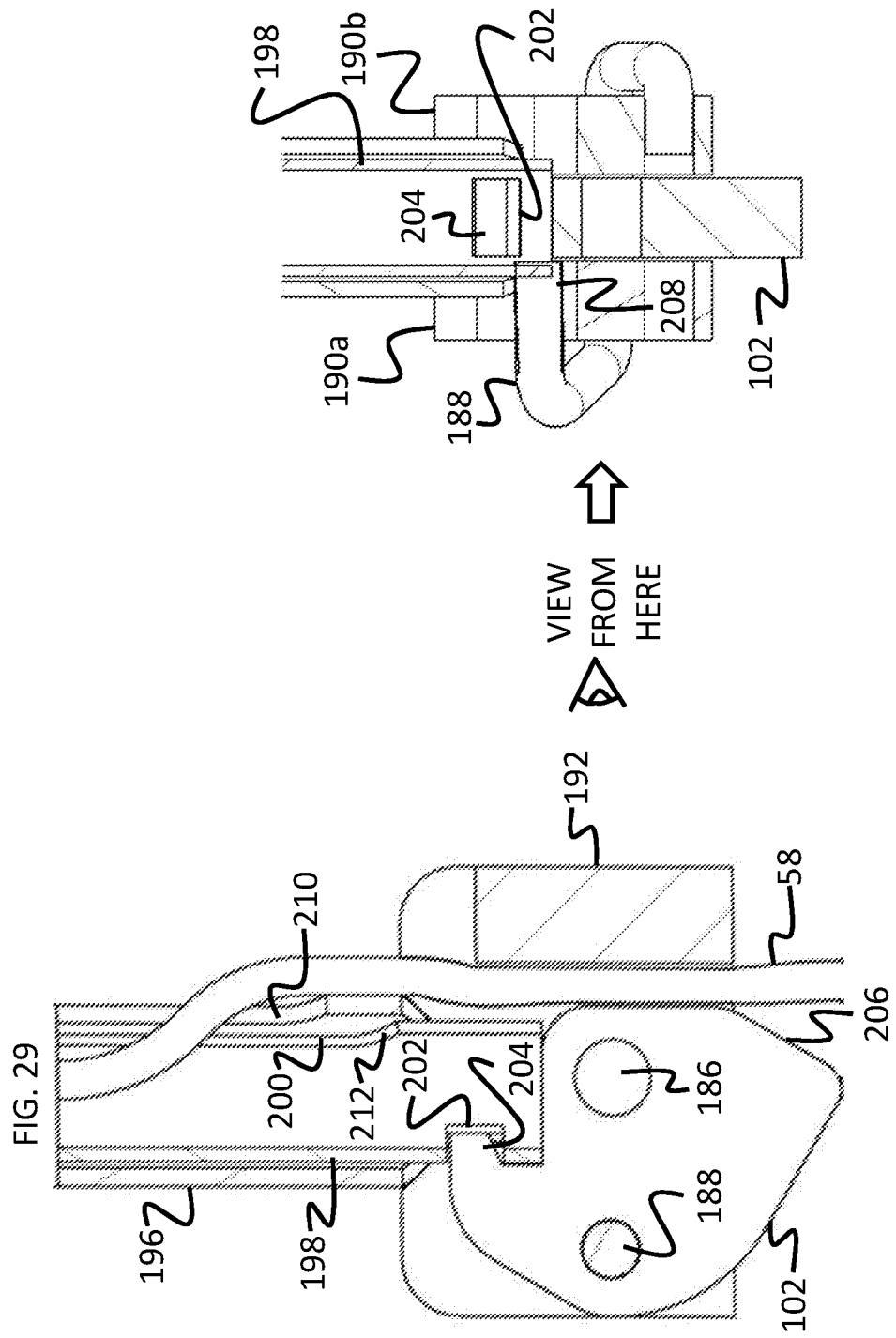

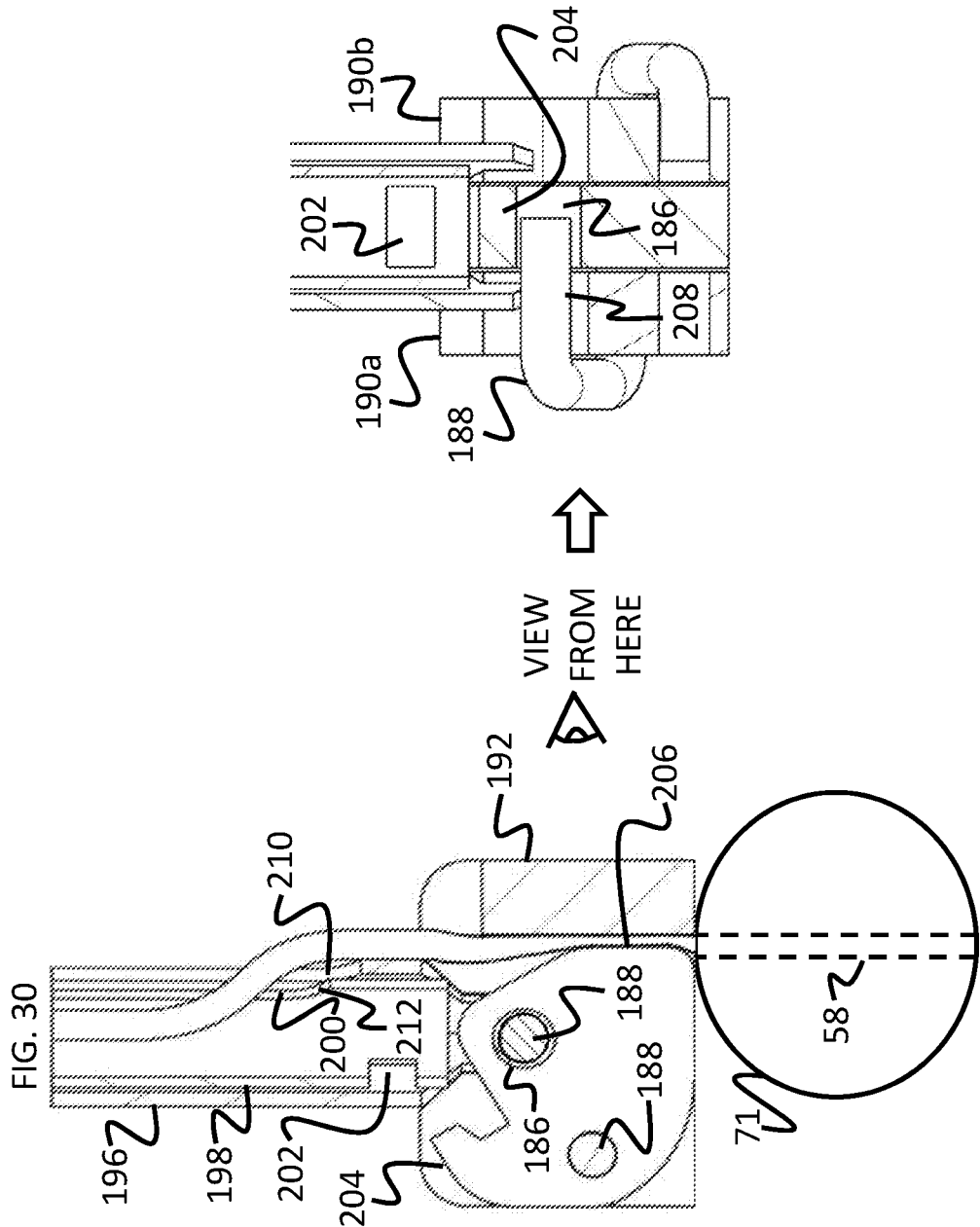

ANCHORS AND LOCKS FOR PERCUTANEOUS VALVE IMPLANTS

CROSS-REFERENCE TO RELATED APPLICATIONS

The present application claims the benefit of U.S. Provisional Application 62/791,912, entitled "Transecatheter ring and valve system," filed Jan. 14, 2019, whose disclosure is incorporated herein by reference.

FIELD OF THE INVENTION

Embodiments of the present invention relate generally to the field of medical devices, and particularly, to apparatus and methods for percutaneous valve repair and replacement.

BACKGROUND

In some subjects, an implant may be used to repair or replace an intracardiac valve.

U.S. Pat. No. 10,278,820 to Bar et al., whose disclosure is incorporated herein by reference, describes an apparatus that includes an assembly of tubes, each one of the tubes being shaped to define a tube lumen. The apparatus further includes a plurality of tissue anchors, each one of the tissue anchors being disposed within a respective one of the tube lumens, an expandable annular structure, including a plurality of teeth, coupled to the assembly of tubes, and a plurality of control wires coupled to the annular structure, configured to position the tubes for deployment of the tissue anchors from the tube lumens, by manipulating the annular structure.

U.S. Pat. No. 10,463,486 to Bar et al., whose disclosure is incorporated herein by reference, describes an apparatus including a plurality of flexible tube guides, an annular assembly of tubes, each of the tubes being slidably disposed within a respective one of the tube guides, a plurality of threads, each of which comprising a distal end that is carried by a respective one of the tubes, and an expandable annular structure coupled to the tube guides, configured to expand the assembly of tubes, from a collapsed configuration, over tissue of a subject, by moving the tube guides radially outward. The apparatus further includes a plurality of control wires coupled to the tube guides, configured to position the tubes, subsequently to the expansion of the assembly, for deployment of the threads from the tubes and into the tissue, by flexing the tube guides.

SUMMARY OF THE INVENTION

There is provided, in accordance with some embodiments of the present invention, an apparatus including a thread and a tissue anchor coupled to the thread. The tissue anchor includes a proximal portion, shaped to define one or more appendages, a distal portion, and a plurality of strips joining the proximal portion to the distal portion. The anchor is configured to anchor the thread at tissue of a subject by virtue of the appendages expanding radially, and the strips expanding radially to form respective loops at a distal side of the tissue, upon removal of a radially-constraining force from the anchor.

In some embodiments, the strips are configured to expand such that the loops are arranged in a circular formation.

In some embodiments, the appendages include respective prongs.

In some embodiments, the thread passes at least partly through the anchor.

In some embodiments, the anchor is coupled to the thread by virtue of the thread being knotted distally to the anchor.

In some embodiments, the anchor is coupled to the thread by virtue of the thread being attached to the distal portion of the anchor.

In some embodiments, the strips consist of 2-8 strips.

In some embodiments, for each of the strips, a circumferential angle between a proximal end of the strip and a distal end of the strip is at least 5 degrees.

In some embodiments, the circumferential angle is between 10 and 30 degrees.

In some embodiments, the proximal portion of the anchor is shaped to define the appendages by virtue of being shaped to define respective grooves beneath the appendages.

In some embodiments, prior to the removal of the constraining force, the appendages do not extend radially more than does any other portion of the anchor.

In some embodiments, following the expansion of the appendages, an angle between each of the appendages and a longitudinal axis of the proximal portion of the anchor is between 5 and 60 degrees.

There is further provided, in accordance with some embodiments of the present invention, a method for anchoring a thread at tissue of a subject. The method includes delivering a tissue anchor, which is radially constrained within a tube and is coupled to the thread, to the tissue. The method further includes passing the tube through the tissue, and subsequently to passing the tube through the tissue, pushing the anchor from the tube such that one or more appendages at a proximal portion of the anchor expand radially, and a plurality of strips, which join the proximal portion of the anchor to a distal portion of the anchor, expand radially to form respective loops at a distal side of the tissue.

In some embodiments, pushing the anchor from the tube includes pushing the anchor from the tube such that the appendages expand at a proximal side of the tissue.

In some embodiments, pushing the anchor from the tube includes pushing the anchor from the tube such that the appendages expand within the tissue.

In some embodiments, the thread passes through the anchor.

In some embodiments, the anchor is coupled to the thread by virtue of the thread being knotted distally to the anchor.

There is further provided, in accordance with some embodiments of the present invention, an apparatus configured to lock an intrabody implant over a thread passing through the implant. The apparatus includes a lock body configured to advance to the implant over the thread and including at least one rotatable element, the lock body being configured to grip the thread proximally to the implant upon rotation of the rotatable element. The apparatus further includes a rotation-maintaining element, configured to inhibit a reversal of the rotation of the rotatable element by engaging with the lock body.

In some embodiments, the lock body includes a jagged surface, and the lock body is configured to grip the thread with the jagged surface.

In some embodiments, the rotatable element includes the jagged surface.

In some embodiments, the lock body further includes a block, and the lock body is configured to grip the thread between the rotatable element and the block.

In some embodiments,
the block is shaped to define a depression, the rotatable element is shaped to define a protrusion configured to fit into the depression upon the rotation of the rotatable element, and the lock body is configured to grip the thread between the protrusion and the depression.

In some embodiments, the at least one rotatable element includes a pair of opposing rotatable elements, and the lock body is configured to grip the thread between the pair of opposing rotatable elements.

In some embodiments, the rotation-maintaining element includes a ring, configured to cause the rotatable element to rotate, and to inhibit the reversal of the rotation, by fitting over the lock body.

In some embodiments, the lock body is shaped to define one or more notches, and the ring is shaped to define respective tabs configured to fit into the notches.

In some embodiments, the ring is configured to cause the rotatable element to rotate by fitting over the rotatable element.

In some embodiments, the apparatus further includes:
a hollow outer longitudinal element, configured to push the ring onto the rotatable element; and
a hollow inner longitudinal element, configured to advance the lock body over the thread while the thread passes through the inner longitudinal element and the inner longitudinal element passes through the outer longitudinal element, prior to the pushing of the ring onto the rotatable element.

In some embodiments,
the inner longitudinal element shaped to define an aperture, and
the ring is shaped to define a tab configured to fit into the aperture while the lock body is advanced over the thread.

In some embodiments, the inner longitudinal element includes a sharp distal edge configured to cut the thread subsequently to the pushing of the ring onto the rotatable element.

In some embodiments, the lock body further includes a shaft disposed next to the rotatable element, and the ring is configured to cause the rotatable element to rotate by fitting over the shaft such that the ring pushes the rotatable element.

In some embodiments,
the shaft is shaped to define a slanted slot,
the lock body further includes:
a first pin coupled to the rotatable element and passing through the slot;
a block; and
a second pint passing rough the rotatable element and through the block, the rotatable element being configured to rotate with respect to the second pin, and by virtue of motion of the first pin being constrained by the slot, the ring is configured to cause the block to be pulled toward the shaft by causing the rotatable element to rotate, such that the lock body grips the thread between the block and the shaft.

In some embodiments, the shaft is shaped to define an aperture, and the ring is shaped to define a tab configured to fit into the aperture.

In some embodiments, the apparatus further includes:
a hollow inner longitudinal element, configured to push the ring onto the shaft; and
a hollow outer longitudinal element, configured to advance the lock body over the thread while the thread passes through the inner longitudinal element and the inner longitudinal element passes through the outer longitudinal element.

In some embodiments, the outer longitudinal element is configured to hold the lock body while advancing the lock body over the thread.

In some embodiments,
the outer longitudinal element includes:
an outer tube; and
an appendage, which is shaped to define an aperture, coupled to and extending from a distal end of the outer tube,
the block is shaped to define a protrusion, and
the outer longitudinal element is configured to hold the lock body by virtue of the protrusion passing through the aperture.

In some embodiments, the appendage is tubular.

In some embodiments, the ring is configured to release the lock body from the outer longitudinal element by causing the block to be pulled toward the shaft such that the protrusion is pulled from the aperture.

In some embodiments,
the inner longitudinal element includes:
an inner tube; and
a ring-pushing appendage, which s shaped to define a side opening, coupled to and extending beyond a distal end of the inner tube, and
the inner longitudinal element is configured to push the ring onto the shaft while the ring-pushing appendage contacts the ring and the thread passes through the inner tube via the side opening.

In some embodiments, the ring-pushing appendage includes a sharp edge configured to cut the thread subsequently to the pushing of the ring onto the shaft.

In some embodiments, the rotation-maintaining element includes a spring.

In some embodiments, the spring includes a coil coiled around the rotatable element and configured to cause the rotatable element to rotate, and to inhibit the reversal of the rotation, by pushing the rotatable element.

In some embodiments, the at least one rotatable element includes a pair of opposing rotatable elements, and the pair are configured to grip the thread between respective proximal ends thereof.

In some embodiments, the apparatus further includes:
a hollow inner longitudinal element including a distal end configured to interpose between the respective proximal ends of the pair while the lock body is advanced to the implant and while the thread passes through the inner longitudinal element; and
a hollow outer longitudinal element, configured to apply a counterforce to the lock body while the inner longitudinal element passes through the outer longitudinal element and while the distal end of the inner longitudinal element is withdrawn from between the respective proximal ends of the pair, such that the pair rotate toward one another by virtue of the coil pushing the pair together.

In some embodiments, the outer longitudinal element includes a sharp distal edge configured to cut the thread subsequently to the rotation of the pair.

In some embodiments, the respective proximal ends of the rotatable elements are shaped to define respective notches, and the distal end of the inner longitudinal element is configured to fit into the notches.

In some embodiments, the rotatable element is shaped to define an aperture, and the spring includes a wire configured to spring into the aperture following the rotation of the rotatable element, thus inhibiting the reversal of the rotation.

In some embodiments, the apparatus further includes:

a hollow inner longitudinal element, configured to rotate the rotatable element by withdrawing from the lock body while the thread passes through the inner longitudinal element; and a hollow outer longitudinal element, configured to apply a counterforce to the lock body while the inner longitudinal element passes through the outer longitudinal element and while the inner longitudinal element is withdrawn from the lock body.

In some embodiments, a distal end of the inner longitudinal element is shaped to define a distal-end aperture, and the rotatable element is shaped to define a protrusion configured to fit inside the distal-end aperture while the lock body is advanced to the implant.

In some embodiments, the inner longitudinal element is shaped to define a side opening, and the inner longitudinal element is configured to advance the lock body to the implant while the thread passes through the inner longitudinal element via the side opening.

In some embodiments, the inner longitudinal element includes a sharp edge at least partly surrounding the side opening and configured to cut the thread upon the withdrawal of the inner longitudinal element.

There is further provided, in accordance with some embodiments of the present invention, a method for locking an intrabody implant over a thread passing through the implant. The method includes advancing a lock body, which includes at least one rotatable element, to the implant over the thread. The method further includes, subsequently to advancing the lock body to the implant, rotating the rotatable element such that the lock body grips the thread proximally to the implant.

The present invention will be more fully understood from the following detailed description of embodiments thereof, taken together with the drawings, in which:

BRIEF DESCRIPTION OF THE DRAWINGS

FIG. 3 is a schematic illustration of a longitudinal cross section through a tube and a tube guide, in accordance with some embodiments of the present invention;

FIG. 4 is a schematic illustration of an alternate thread-deployment apparatus, in accordance with some embodiments of the present invention;

FIG. 5 is a schematic illustration of a thread-deploying element, in accordance with some embodiments of the present invention;

FIGS. 6A-D collectively show the deployment of a thread into tissue by a thread-deploying element, in accordance with some embodiments of the present invention;

FIG. 12 is a schematic illustration of a tissue anchor an expanded state, in accordance with some embodiments of the present invention;

FIG. 13 is a schematic illustration of a tissue anchor anchoring a thread at tissue of a subject, in accordance with some embodiments of the present invention;

FIG. 14 is a schematic illustration of a lock, in accordance with some embodiments of the present invention;

FIGS. 15A-B are schematic illustrations of longitudinal cross-sections through the lock of FIG. 14, in accordance with different respective embodiments of the present invention;

FIG. 16A is a schematic illustration of a locking device for locking a lock over an implant, in accordance with some embodiments of the present invention;

FIG. 16B is a schematic illustration of a longitudinal cross-section through part of the locking device of FIG. 16A, in accordance with some embodiments of the present invention;

FIG. 17 is a schematic illustration of an advancing of a lock body over a thread, in accordance with some embodiments of the present invention;

FIG. 18 is a schematic illustration of a pushing of a ring onto a lock body, in accordance with some embodiments of the present invention;

FIG. 19 is a schematic illustration of a lock, in accordance with some embodiments of the present invention;

FIG. 20A is a schematic illustration of a locking device for locking a lock over an implant, in accordance with some embodiments of the present invention;

FIG. 20B is a schematic illustration of a longitudinal cross-section through part of the locking device of FIG. 20A, in accordance with some embodiments of the present invention;

FIG. 25 is a schematic illustration of an advancing of a lock over a thread, in accordance with some embodiments of the present invention;

FIG. 26 is a schematic illustration of a locking of a lock, in accordance with some embodiments of the present invention;

FIG. 27 is a schematic illustration of a lock, in accordance with some embodiments of the present invention;

FIG. 28A is a schematic illustration of a locking device for locking a lock over an implant, in accordance with some embodiments of the present invention;

FIG. 28B shows a longitudinal cross-section through a portion of the locking device of FIG. 28A, in accordance with some embodiments of the present invention;

FIG. 29 is a schematic illustration of an advancing of a lock over a thread, in accordance with some embodiments of the present invention; and FIG. 30 is a schematic illustration of a locking of a lock, in accordance with some embodiments of the present invention.

DETAILED DESCRIPTION OF EMBODIMENTS

Overview

Embodiments of the present invention provide apparatuses and methods for the percutaneous implantation of annuloplasty valves and other implants.

In embodiments of the present invention, one or more threads are deployed at an implantation site within the body of a subject, such as at the subject's mitral valve annulus. Subsequently, an implant, such as an annuloplasty valve, is advanced (or "delivered") over the threads to the implantation site. Next, respective locks are advanced, over the threads, to the implant, and are locked proximally to the implant. Upon the locking of the locks, the locks grip the threads, thus locking the implant in place. Following the locking of the implant, the threads are cut proximally to the locks.

In some embodiments, respective tissue anchors, which are coupled to the threads, are expanded at the tissue of the implantation site during the deployment of the threads, such that the anchors anchor the threads to the tissue. One particular type of anchor described herein comprises a tube made of a shape-memory material and comprising a plurality of strips joining the proximal portion of the tube to the distal portion of the tube, together with one or more appendages at the proximal portion of the tube. Upon the deployment of the anchor, the strips expand radially to form respective loops at the distal side of the tissue, and the appendages expand radially within the tissue or at the proximal side of the tissue. Advantageously, the loops inhibit the anchor (and hence the thread) from migrating proximally from the tissue while also distributing the stress applied to the tissue, while the appendages inhibit the anchor (and hence the thread) from migrating distally from the tissue.

In other embodiments, the threads are looped through the tissue, such that tissue anchors may not be required.

Embodiments of the present invention also include various types of locks. Each of the locks comprises at least one rotatable element and is configured to grip a thread upon rotation of the rotatable element. For example, upon the rotation of the rotatable element, the rotatable element may press the thread against another portion of the lock. Each lock further comprises a rotation-maintaining element configured to maintain the rotatable element in its rotated position, and hence maintain the gripping of the thread. For example, the lock may comprise a ring that, by fitting over the rotatable element or another part of the lock, inhibits the rotatable element from rotating backward.

Thread Deployment and Implant Delivery

Figure 1:
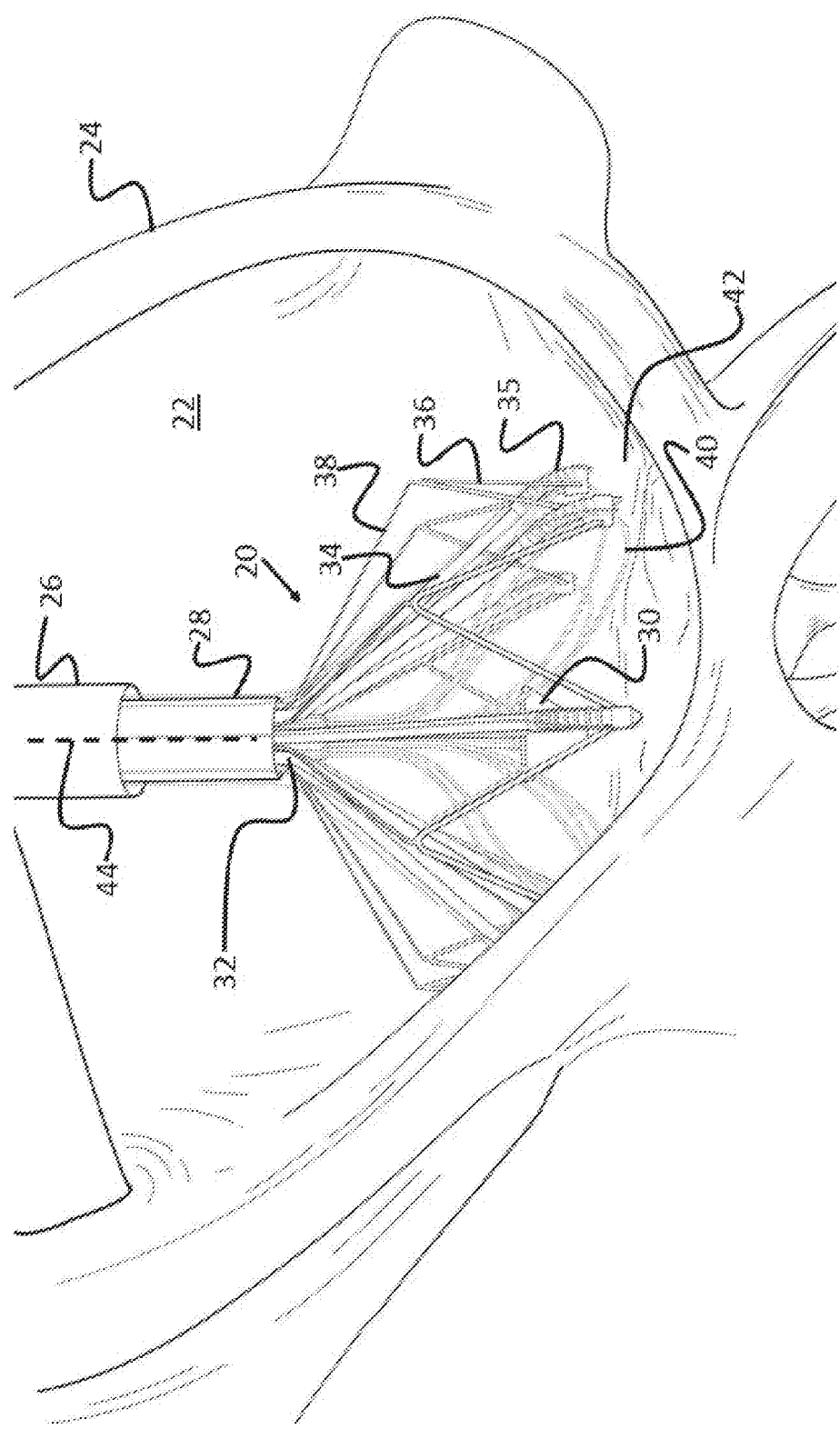
FIG. 1 is a schematic illustration of a thread-deployment apparatus deployed within a left atrium of a heart of a subject, in accordance with some embodiments of the present invention.

Reference is initially made to FIG. 1, which is a schematic illustration of a thread-deployment apparatus 20 deployed within a left atrium 22 of a heart 24 of a subject, in accordance with some embodiments of the present invention.

To deliver thread-deployment apparatus 20 to left atrium 22, a sheath 26 is first inserted, percutaneously, into heart 24, e.g., via the femoral vein and inferior vena cava, or via the jugular vein and superior vena cava. Subsequently, techniques known in the art are used to pass sheath 26 through the interatrial septum and into the left atrium. Sheath 26 is typically advanced over a guidewire, under fluoroscopic guidance, and/or under the guidance of any other suitable imaging modality, such as ultrasound (e.g., transthoracic echocardiography (TTE) or transesophageal echocardiography (TEE)), magnetic resonance imaging (MRI), or computed tomography (CT).

Subsequently to delivery of the sheath to the left atrium, apparatus 20 is advanced distally from sheath 26. In some embodiments, a catheter 28 is first advanced from the sheath, and apparatus 20 is then pushed through catheter 28, emerging from the distal end of the catheter.

In some embodiments, as shown in FIG. 1, sheath 26 is flexed within the left atrium, such that the distal opening of sheath 26 faces the mitral valve. Catheter 28 is similarly flexed. Subsequently, apparatus 20 is pushed, from the distal opening of catheter 28, toward the mitral valve. Alternatively, for embodiments in which sheath 26 is flexed within the left atrium, catheter 28 may not be required, and apparatus 20 may be held by and pushed from sheath 26.

In other embodiments, sheath 26 is not flexed within the left atrium; rather, catheter 28 is flexed subsequently to being advanced from the sheath, such that the opening of the catheter faces the mitral valve. Apparatus 20 is then advanced from the catheter.

Initially, apparatus 20 is in a collapsed, or "crimped," state. In some embodiments, a retaining tip 30, which initially covers the distal end of apparatus 20, holds the apparatus in this collapsed state, Subsequently to the distal advancement of apparatus 20 from sheath 26, retaining tip 30 is pushed off of the distal end of the apparatus, using a pushing wire that passes, from the retaining tip, through the length of sheath 26 to the exterior of the subject. Apparatus 20 may then expand (or "open") within the atrium. Additionally to the removal of retaining tip 30, a slider 32 may be used to open the apparatus, as further described below with reference to FIG. 2. Alternatively to using slider 32, a covering sheath may be retracted from over the apparatus.

Apparatus 20 comprises an annular assembly (or "collection") of tubes 34, along with a plurality of flexible tube guides 35. Each of tubes 34 is slidably disposed within a respective tube guide 35, such that the tube guide guides the movement of the tube. Typically, each of the tube guides is cylindrical in shape.

Apparatus 20 further comprises an expandable annular structure 36, which is coupled to the tube guides. In some embodiments, annular structure 36 is manufactured from a suitable shape-memory material, e.g., Nitinol. The pushing-off of retaining tip 30, and/or the appropriate movement of slider 32, allows annular structure 36 to expand, such that annular structure 36 expands radially-outward towards its predetermined, "remembered" shape. In other embodiments, annular structure 36 is manufactured from a non-shape-memory material, such as stainless steel, polymeric tubing, and/or any other suitable metals, polymers, or combinations thereof. In such embodiments, the pushing-off if retaining tip 30, and/or the appropriate movement of slider 32, allows annular structure 36 to spring from its crimped state. In any case, as the annular structure expands, the annular structure expands the assembly of tubes over the tissue 42 of the subject, by moving tube guides 35 radially outward.

A plurality of threads (not shown) pass from tubes 34 to the exterior of the subject. Following the expansion of the annular structure (and, hence, of the annular assembly of tubes) within the subject, the tubes are positioned and/or oriented over tissue 42, for the subsequent deployment of the threads from the tubes into tissue 42. For example, the tubes may be positioned over the mitral-valve annulus (i.e., at the top face of the annulus, inside the left atrium), for the subsequent deployment of the threads into the annulus.

In general, apparatus 20 may comprise any suitable number of tubes, such as 4-20 tubes. Tubes 34 may be manufactured from any suitable metal or plastic material. Typically, the tubes pass through the entire length of sheath 26, such that, throughout the delivery, deployment, and subsequent use of apparatus 20, the proximal ends of tubes 34 are positioned outside of the subject. Typically, apparatus 20 is rotatable around a central longitudinal axis 44 of the apparatus.

Typically, apparatus 20 comprises a plurality of longitudinal wires 38, which are coupled to the annular structure, typically at the proximal end (or "top") of the annular structure. As further described below with reference to FIG. 2, longitudinal wires 38 may facilitate adjusting the radius of apparatus 20, thus facilitating the positioning of tubes 34 for the deployment of the threads from the tubes, and/or facilitating the crimping of the apparatus following the deployment of the threads. In some embodiments, longitudinal wires 38 may be further used to manipulate annular structure 36, thus facilitating the positioning of the tubes. For example, by applying a pushing force to the annular structure, longitudinal wires 38 may move annular structure 36 (and hence also the tubes) in the axial direction, i.e., in a direction that is parallel to central longitudinal axis 44, such that each tube is brought into contact with the valve annulus.

Typically, apparatus 20 further comprises a plurality of control wires 40, which are coupled to the respective distal portions of tube guides 35. Control wires 40 are configured to flex the tube guides, thus positioning and/or orienting the tubes for the subsequent deployment of the threads. For example, as described with reference to FIGS. 12A-D of U.S. Pat. No. 10,463,486 to Bar et. al, to move a thread-deployment position radially inward (i.e., toward axis 44), the relevant tube may be flexed radially inward; conversely, to move the thread-deployment position radially outward, the relevant tube may be flexed radially outward.

Following any necessary positioning and/or orienting of any particular tube 34, the tube is pushed through the tube guide within which the tube is contained, such that the tube penetrates tissue 42. Subsequently, the thread is deployed from the tube, i.e., the thread is passed from within the tube or from the outer surface of the tube and through the tissue, as further described below with reference to FIG. 3. (The thread may be passed from the outer surface of the tube by retracting the tube, and/or by pushing an anchor, to which the thread is coupled, from the outer surface of the tube.)

Although FIG. 1 shows the deployment of apparatus 20 specifically within a left atrium, it is noted that apparatus 20 may be similarly deployed at other suitable location within the body of the subject. For example, apparatus 20 may be deployed within the right atrium of the subject, to facilitate the delivery of threads to the tricuspid-valve annulus.

Figure 2:
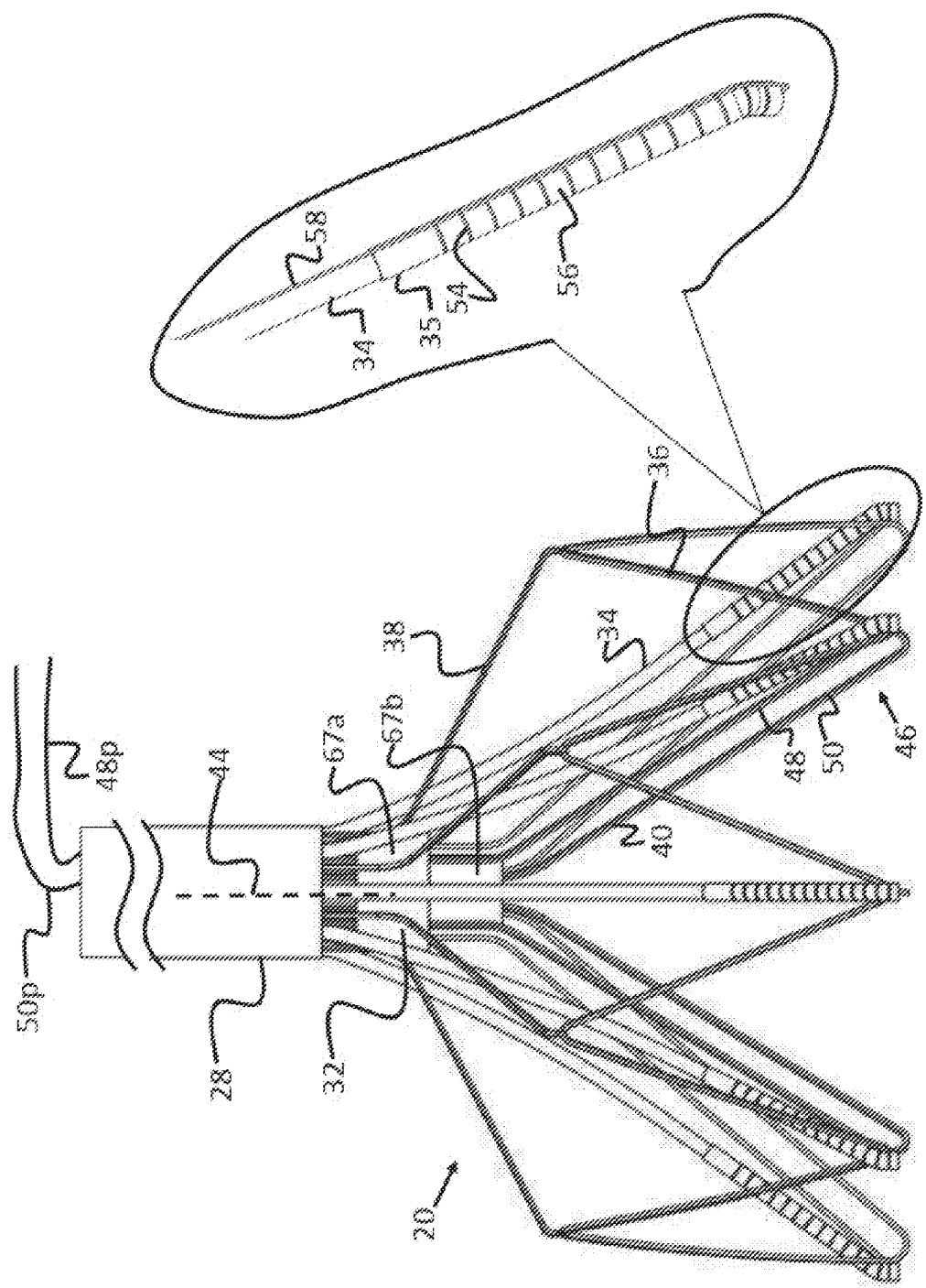
FIG. 2 is a schematic illustration of a thread-deployment apparatus in its expanded state, in accordance with some embodiments of the present invention.

Reference is now made to FIG. 2, which is a schematic illustration of thread-deployment apparatus 20 in its expanded state, in accordance with some embodiments of the present invention.

Reference is first made to the inset portion of FIG. 2, which shows a tube 34 passing partly through a tube guide 35, along with a thread 58 passing from the distal end of the tube guide.

As described above with reference to FIG. 1, tube guide 35 is flexible. For example, tube guide 35 may be shaped to define a plurality of circumferential grooves 54. For example, each groove 54 may extend for at least 50%, such as at least 65%, of the circumference of tube guide 35, such that tube guide 35 is divided, by the grooves, into a plurality of semi-connected segments 56. In such embodiments, tube guide 35 is flexible by virtue of grooves 54, in that segments 56 may swivel relative to each other. Alternatively, tube guide 35 may be flexible by virtue of the material from which the tube guide is made, and/or by virtue of any suitable manufacturing process. In general, tube guide 35 may be manufactured from any suitable plastic or metal material, such as Nitinol.

As described above with reference to FIG. 1, tube guides 35 guide the passage of the tubes, thus facilitating the deployment of threads 58 from the tubes. In some embodiments, prior to threads 58 being deployed, the distal ends of threads 58 are carried inside tubes 34, as further described below with reference to FIG. 3. In such embodiments, threads 58 may pass through the distal ends of tube guides 35, and then run along the outside of tube guides 35 and tubes 34 to the exterior of the subject. Alternatively, instead of passing through the distal ends of the tube guides, threads 58 may pass through apertures in the walls of the tubes, and/or apertures in the walls of the tube guide. As yet another alternative, threads 58 may run inside tubes 34 to the exterior of the subject.

In other embodiments, prior to threads 58 being deployed, the distal ends of threads 58 are carried on the outside surface of tubes 34. For ease of description, however, the remainder of the present description generally assumes that the distal ends of the threads are carried inside tubes 34, as shown in FIG. 2.

Typically, each one of the tube guides is coupled to at least one control wire 40. In some embodiments, as shown in FIG. 2, each of control wires 40 comprises a looped distal end 46, which is coupled to a respective one of the tube guides. Typically, looped distal end 46 is radially-oriented, such that an outer arm 48 of the looped distal end, which is closer to the tube and tube guide, is disposed at a first radius, and an inner arm 50 of the looped distal end, which is further from the tube and tube guide, is disposed at a second radius that is smaller than the first radius. (In this context, the "radius" refers to the distance from axis 44.)

(It is noted that outer arm 48 and inner arm 50 may also be said to belong to the entire control wire, rather than only to looped distal end 46. Thus, for example, it may be said that outer arm 48 and inner arm 50 extend from looped distal end 46 to the exterior of the subject.)

In some embodiments, control wires 40 are directly coupled to the tube guides. In other embodiments, the control wires are indirectly coupled to the tube guides, in that, for example, the control wires are coupled to annular structure 36, which is in turn coupled to the tube guides. It is noted that, in the context of the present application, including the claims, the term "coupled" may include, within it scope, either a direct coupling or an indirect coupling.

Typically, for embodiments in which the control wires are looped, each tube guide is flexed by moving one proximal end of the attached control wire with respect to the other proximal end of the control wire. For example, the proximal end 50*p* of inner arm 50 may be pulled or pushed while the proximal end 48*p* of outer arm 48 is held in place or allowed to freely slide; alternatively, proximal end 48*p* may be pulled or pushed while proximal end 50*p* is held in place or allowed to freely slide. The flexing of the tube guides facilitates positioning the tubes, as described with reference to FIGS. 12A-D of U.S. Pat. No. 10,463,486 to Bar et al.

In other embodiments, the control wires are not looped, but rather, are longitudinal, similarly to longitudinal wires 38. Typically, in such embodiments, each tube is coupled to two control wires, with one of the two control wires disposed at a greater radius than the other control wire. (In such embodiments, the outer control wire is analogous to outer arm 48, and hence may be referred to as the "outer control arm," while the inner control wire is analogous to inner arm 50, and hence may be referred to as the "inner control arm.") The two control wires may be coupled to a common point on the tube guide. Alternatively, the outer control wire may be coupled at a slightly more proximal position than the inner control wire. For example, the two control wires may be coupled, respectively, to two different segments 56 belonging to the tube, at a distance of 0.5-10 mm from one another.

In yet other embodiments, a single longitudinal control wire is coupled to each one of the tube guides. In such embodiments, each tube guide may be flexed by moving the attached control wire relative to the tube that passes through the tube guide.

As described above with reference to FIG. 1, slider 32 may be used to expand (i.e., open) and crimp (i.e., close) both the assembly of tubes 34 and annular structure 36. Typically, slider 32 slides along a "track" that is formed by control wires 40; for example, slider 32 may slide along both inner arms 50 and outer arms 48 of the control wires. When the slider is at (or near) its most distal position on this track, the assembly of tubes, and the annular structure, are held in a crimped position. Hence, to crimp the apparatus, slider 32 may be slid distally along the control wires, such that the slider exerts a crimping force on the tube assembly and the annular structure. Subsequently to the distal sliding of the slider, catheter 28 and; or sheath 26 may be slid distally along longitudinal wires 38, thus further crimping the apparatus. Finally, catheter 28 and/or sheath 26 may be passed over the apparatus. Conversely, to expand the apparatus, slider 32 may be slid proximally along the control wires, such as to allow the annular structure, and hence also the assembly of tubes, to expand.

Typically, each inner arm passes through the slider a ta radius that is smaller than the radius at which the corresponding outer arm passes through the slider. For example, slider 32 may comprise a first cylinder 67*a*, through which the respective outer arms of the control wires pass, and a second cylinder 67*b*, disposed distally from, and being narrower than (i.e., having a smaller radius than), first cylinder 67*a*, through which the respective inner arms of the control wires pass. This configuration facilitates the crimping of the apparatus, in that slider 32 may slide to a more distal position than might otherwise be possible.

Typically, annular structure 36 comprises a triangular-wave-shaped ring having alternating top and bottom vertices, each of the bottom vertices being coupled to a respective one of the tube guides. In such embodiments, longitudinal wires 38 are typically coupled to the top vertices of the annular structure. As described above, longitudinal wires 38 facilitate adjusting the radius of apparatus 20, in that the radius may be adjusted by sliding catheter 28 (and/or sheath 26) along the longitudinal wires. This adjustment may facilitate the positioning of tubes 34 for the deployment of the threads from the tubes, and/or the crimping of the apparatus following the deployment of the threads.

Reference is now made to FIG. 3, which is a schematic illustration of a longitudinal cross section through a tube 34 and a tube guide 35, in accordance with some embodiments of the present invention.

Typically, a plurality of expandable tissue anchors 60 are disposed, respectively, within tubes 34. In addition, a plurality of anchor-pushing elements 62 are disposed, respectively, within the tubes, proximally to anchors 60.

Figure 10:
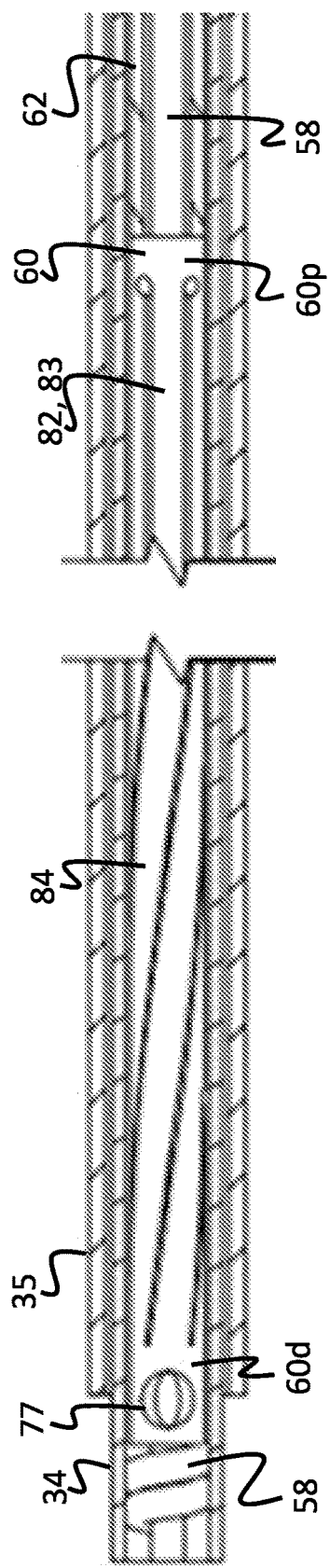
FIG. 10 is a schematic illustration of a tissue anchor held within a tube, in accordance with some embodiments of the present invention.

In some embodiments, as shown in FIG. 3, the distal end of each thread 58 is tied to a respective anchor 60. In such embodiments, as shown in FIG. 3, thread 58 may pass through the distal end of the tube and of the tube guide, and run alongside tube 34 to the exterior of the subject; alternatively, the thread may pass through the tube. In other embodiments, the thread is coupled to the anchor by virtue of passing through the anchor and being knotted distally to the anchor (such that the diameter of the knot is greater than the diameter of the anchor). In such embodiments, typically, the thread passes through the tube, e.g., by virtue of passing through anchor-pushing element 62, as shown in FIG. 10 (described below).

Figure 9:
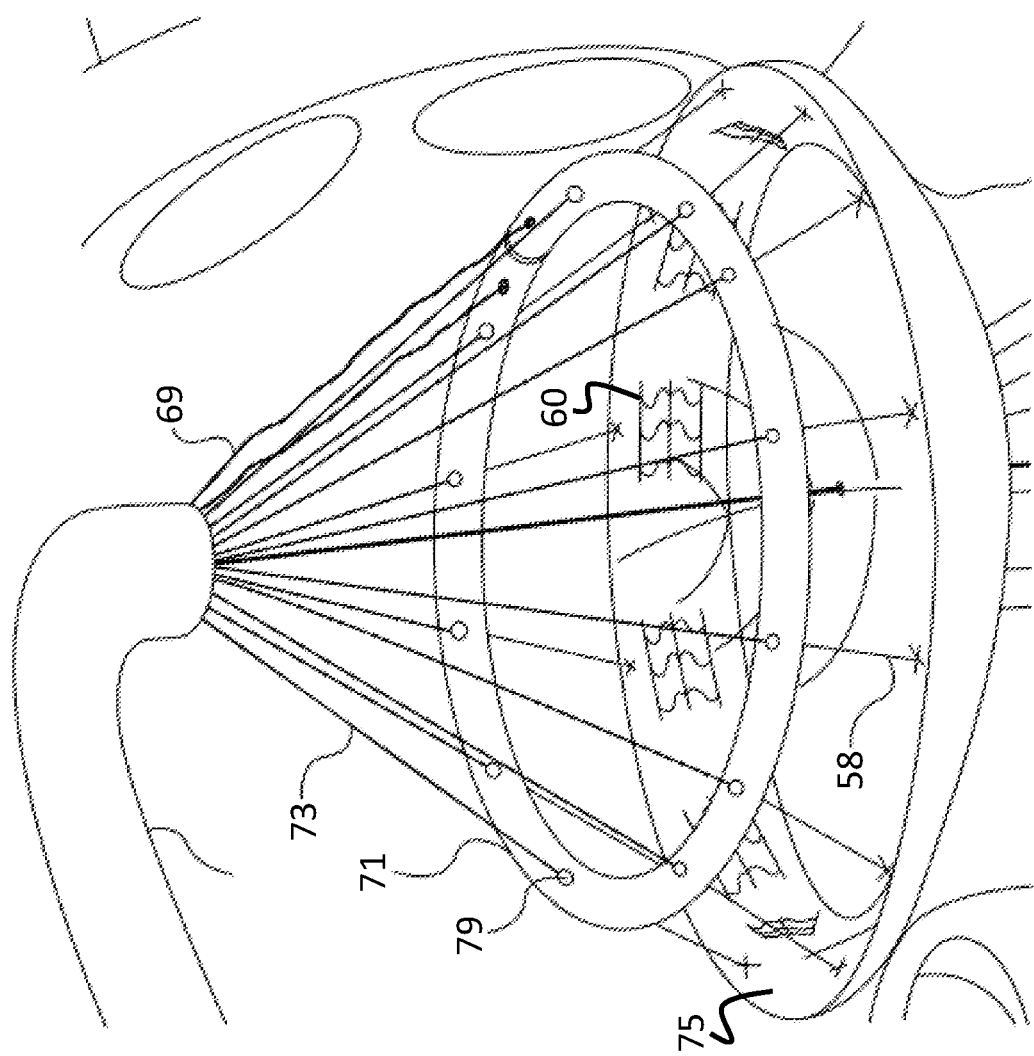
FIG. 9 is a schematic illustration of a delivery of an implant to a mitral-valve annulus, in accordance with some embodiments of the present invention.

To deploy a particular thread, the tube that carries the thread is passed through the tissue, such that the thread is also passed through the tissue. (Tubes 34 may extend to the exterior of the subject, in which case the tubes may be pushed directly; alternatively, separate tube-pushing elements, which are disposed proximally to the tubes and extend to the exterior of the subject, may be used to push the tubes.) Subsequently, anchor 60 is pushed from the tube, using anchor-pushing element 62. Upon exiting from the tube, anchor 60 expands at the far side of the tissue, e.g., as shown in FIG. 9 and in FIG. 13. Subsequently, the tube and anchor-pushing element are retracted into tube guide 35.

Subsequently to the deployment of anchor 60, a pulling force may be continuously applied to thread 58 to hold anchor 60 in place until the implant is locked in place, e.g., as described below with reference to FIGS. 14-30. Alternatively or additionally, the anchor ay comprise one or more appendages, which facilitate holding the anchor in place by engaging with the tissue, e.g., as described below with reference to FIG. 13.

In some embodiments, as shown in FIG. 3, each tube 34 comprises a pointed distal end 64. In such embodiments, tubes 34 may alternatively be referred to as "needles," and tube guides 35 as "needle guides." In some embodiments, tube 34 is distally coupled to a needle, comprising distal end 64. In the context of the present application, including the claims, such a needle may be considered an extension of the tube.

As described above with reference to FIG. 1 tubes 34 may be positioned at the top face of the mitral-valve annulus, within the left atrium. In some embodiments, to deploy anchors 60, tubes 34 are passed through the annulus and into the left ventricle, such that anchors 60 expand within the left ventricle, beneath the leaflets of the valve. In other embodiments, the tubes emerge from the tissue above the leaflets of the valve, within the left atrium. In some embodiments, pointed distal end 64 is curved radially inward, such that the tube exits the valve annulus through the radially-inward-facing face of the valve annulus. In such embodiments, the anchors may be deployed along the radially-inward-facing face of the valve annulus, as shown in FIG. 9. (It is noted that in the context of the present application, including the claims, the term "distal side," when used with reference to tissue of the implantation site, may include the radially-inward-facing face of the valve annulus.)

In some embodiments, the tubes penetrate the tissue only after all of the tubes have been appropriately positioned and/or oriented. In other embodiments, at least one of the tubes may penetrate the tissue before all of the tubes have been appropriately positioned and/or oriented, such that the subsequent positioning of the other tubes does not cause the first tube to move from its intended penetration site. For example, the sequence of (i) positioning and/or orienting the tube, (ii) passing the tube through the mitral valve annulus, (iii) passing the tissue anchor from the tube, and (iv) retracting the tube and anchor-pushing element, may be performed one tube at a time, for each of the tubes. Alternatively, for example, after positioning and/or orienting each tube, the tube may penetrate the tissue of the annulus, but the tissue anchors may not be passed from the tube until at least some of the other tubes have also penetrated the tissue.

It is noted that each tube, along with the corresponding tube guide and/or any of the other components described above that facilitate deployment of the thread, may be referred to as a "thread-deploying element," such that apparatus 20 may be referred to as an annular assembly of thread-deploying elements.

Reference is now made to FIG. 4, which is a schematic illustration of an alternate thread-deployment apparatus 20a, in accordance with some embodiments of the present invention.

In general, apparatus 20a is similar to apparatus 20, e.g., with respect to the manner in which expandable annular structure 36 expands the assembly of tubes 34 over the tissue prior to the deployment of the threads, and the manner in which the tubes are positioned and/or oriented, Apparatus 20a differs from apparatus 20, however, with respect to the configuration of tubes 34, and the manner in which the threads are deployed.

In particular, in apparatus 20a, each tube 34 comprises an arced distal portion 66, disposed proximally to tube guide 35. For example, distal portion 66 may be shaped to define a distally-facing crescent, comprising a first tube-end 68a and a second tube-end 68b. In general, arced distal portion 66 is less flexible than more proximal portions of tube 34; for example, arced distal portion 66 may be rigid. (In some embodiments, a portion of tube 34 that is immediately proximal to the arced distal portion may also be rigid.)

As further described below with reference to FIGS. 5 and 7, at least one arced needle is disposed within arced distal portion 66. Each of the arced needles is coupled to the distal end of a respective thread 58 (not shown in FIG. 4), which, as in apparatus 20, may run alongside tube 34, or within tube 34, to the exterior of the subject. As further described below, the arced needles are configured to loop the threads through the tissue of the valve annulus, by arcedly passing, from arced distal portion 66, through the tissue. By virtue of the threads looping through the tissue, it may not be necessary to deploy any anchors.

Typically, first tube-end 68a and second tube-end 68b are pointed. (Thus, as in apparatus 20, tube 34 may be referred to as a "needle," and tube guide 35 may be referred to as a "needle guide.") In such embodiments, to facilitate the deployment of the threads, first tube-end 68a and second tube-end 68b may penetrate the tissue of the annulus, prior to the passing of the arced needle(s) from arced distal portion 66 and through the tissue.

Each tube, along with the arced needle(s) contained therein and/or any of the other components described below that facilitate deployment of the thread(s), may be referred to as a "thread-deploying element," such that apparatus 20a may be referred to as an annular assembly of thread-deploying elements. In this regard, reference is now made to FIG. 5, which is a schematic illustration of a thread-deploying element 65, in accordance with some embodiments of the present invention. (FIG. 5 does not show the portion of tube 34 that is proximal to distal portion 66, or tube guide 35.)

In the particular embodiment shown in FIG. 5, a single arced needle 70, having a pointed distal end 70d, is disposed within arced distal portion 66. Thread 58 is coupled to the proximal end 70p of needle 70. Thread-deploying element 65 comprises one or more (e.g., exactly two) distal shafts 72, which are coupled to the tube in contact with needle 70. As further described below with reference to FIGS. 6A-D, shafts 72 are configured to pass needle 70 through tissue 42, by rotating. Typically, shafts 72 are rotated by rotating one or more proximal shafts 74. For example, one or more belts 76 may, collectively, mechanically couple shafts 72 to each other and to proximal shafts 74, such that distal shafts 72 rotate in response to rotation of the proximal shafts. (It is noted that any shaft that is not in contact with needle 70 is referred to herein as a "proximal shaft," even if the shaft is relatively close to distal portion 66 of the tube.)

Reference is now made to FIGS. 6A-D, which collectively show the deployment of thread 58 into tissue 42 by thread-deploying element 65, in accordance with some embodiments of the present invention.

FIG. 6A shows the penetration of tissue 42 by arced distal portion 66 of tube 34. Following the penetration of the tissue, as shown in FIG. 6B, distal shafts 72 are rotated (via rotation of proximal shafts 74), such that needle 70 arcedly passes, from arced distal portion 66, through tissue 42. (The motion of the needle may also be described as a "rotation.") As the needle passes through the tissue, thread 58, which is coupled to the proximal end of the needle, also passes through the tissue. Typically, the needle is rotated such that the entire needle passes (i) through one of the tube-ends and into the tissue, (ii) through the tissue, and (iii) through the other one of the tube-ends. For example, the needle may undergo a full rotation of 360 degrees.

FIG. 6C shows the configuration of thread-deploying element 65 following the rotation of needle 70. In this configuration, thread 58 arcedly passes through the tissue from one tube-end through the other tube-end, and then, from an aperture in arced distal portion 66, to the exterior of the subject. (For clarity, inn FIG. 6C, the path of thread 58 is emphasized.)

As shown in FIG. 6D, following the rotation of the needle, tube 34 is retracted through the tube guide, such that arced distal portion 66 is withdrawn from the tissue. Following the withdrawal of the thread-deploying element, thread 58 loops through tissue 42, such that, following the withdrawal of apparatus 20a from the body of the subject, two different segments of the thread—a first segment 63a and a second segment 63b—pass from the tissue to the exterior of the subject.

Figure 7:
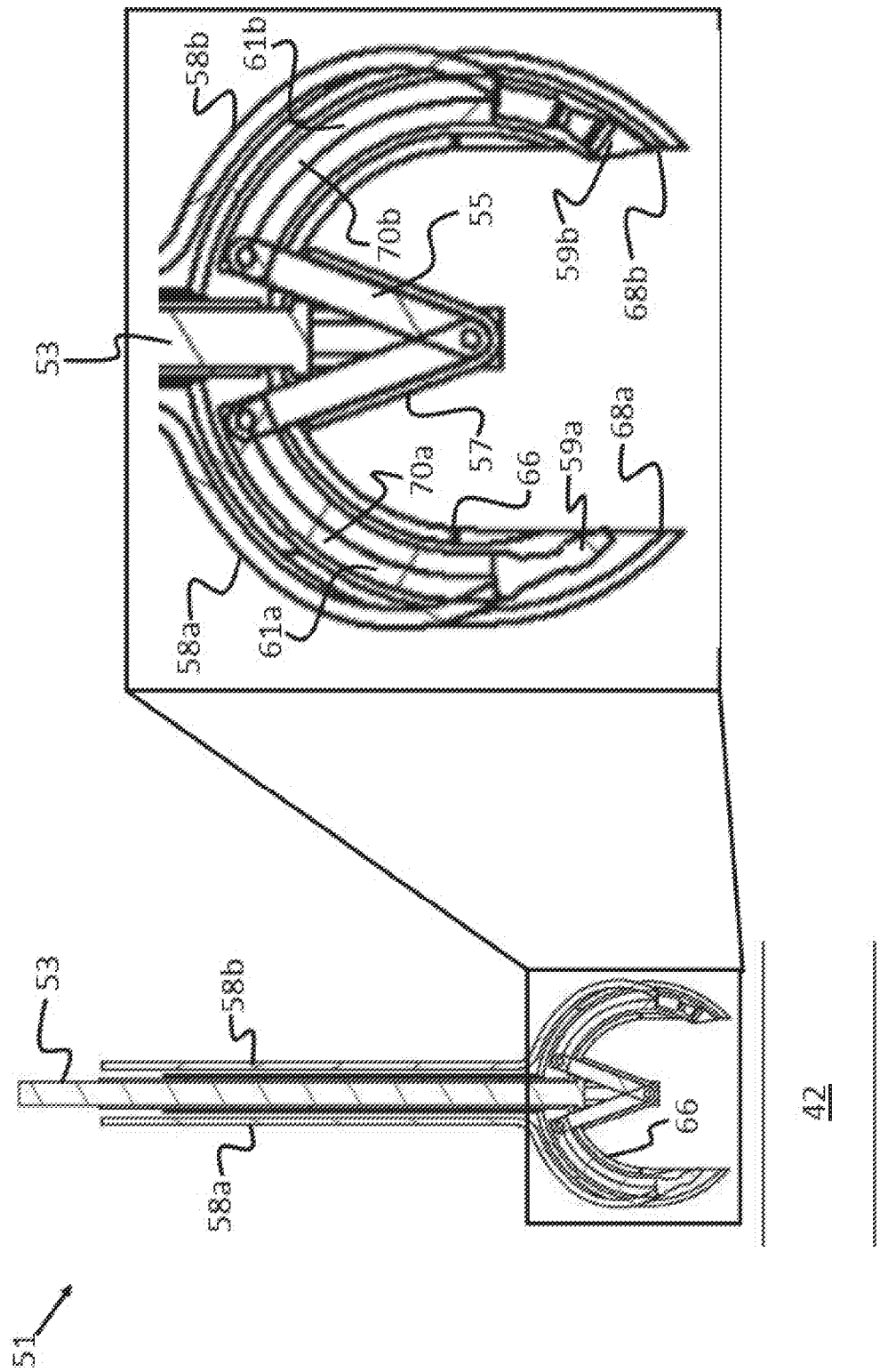
FIG. 7 is a schematic illustration of an alternate thread-deploying element, in accordance some embodiments of the present invention.

Reference is now made to FIG. 7, which is a schematic illustration of an alternate thread-deploying element 51, in accordance with some embodiments of the present invention. (Similarly to FIG. 5, FIG. 7 does not show the entirety of tube 34, or tube guide 35.)

Thread-deploying element 51 may be used with thread-deployment apparatus 20a (FIG. 4), alternatively or additionally to thread-deploying element 65. Thread-deploying element 51 is similar to thread-deploying element 65 in at least some ways. For example, in thread-deploying element 51, tube 34 comprises arced distal portion 66, comprising tube-ends 68a and 68b. Thread-deploying element 51 also differs from thread-deploying element 65 in at least some ways. For example, instead of a single arced needle, thread-deploying element 51 comprises a pair of arced needles, comprising a first arced needle 70a and a second arced needle 70b. Typically, first arced needle 70a comprises a first pointed distal end 59a and a first needle body 61a, which are reversibly coupled to one another. Similarly, second arced needle 70b comprises a second pointed distal end 59b and a second needle body 61b, which are reversibly coupled to one another. A first thread 58a is coupled to first pointed distal end 59a, while a second thread 58b is coupled to second pointed distal end 59b.

As further described below with reference to FIGS. 8A-D, first arced needle 70a and second arced needle 70b deploy first thread 58a and second thread 58b by arcedly passing through tissue 42, toward one another, from, respectively, first tube-end 68a and second tube-end 68b. Upon the two arced needles colliding with one another within the tissue, first pointed distal end 59a and second pointed distal end 59b couple to one another, such that first thread 58a is coupled to second thread 58b. Thus, the two threads effectively become a single thread that loops through the tissue, similarly to the looping of thread 58 shown in FIG. 6D.

Typically, the respective proximal ends of the arced needles are coupled to a hinge 55, which may be controlled by a hinge-control rod 53. Typically, as shown in FIG. 7, hinge 55 is v-shaped, the respective proximal ends of the arced needles being coupled to the respective ends of the hinge, and the distal end of hinge-control rod 53 being disposed inside of the hinge. A spring (or "clamp") 57 applies a closing force to the hinge, such that, when the distal end of hinge-control rod 53 is at a relatively proximal position (as in FIG. 7), the hinge is almost closed, and the arced needles are inside of arced distal portion 66. Conversely, when hinge-control rod 53 is pushed, against the hinge, to a more distal position, the hinge is opened, causing the arced needles to pass from arced distal portion 66 and through the subject's tissue.

First pointed distal end 59a and second pointed distal end 59b may be configured to couple to one another in any suitable way. For example, as shown in FIG. 7, first pointed distal end 59a may be shaped to define a male connecting tip, and second pointed distal end 59b may be shaped to define a female connecting tip configured to fittingly receive first pointed distal end 59a. Upon a sufficient force being applied to hinge 55 by hinge-control rod 53, first pointed distal end 59a is forced into second pointed distal end 59b.

Reference is now made to FIGS. 8A-D, which collectively show the deployment of threads 58a and 58b into tissue 42 by thread-deploying element 51, in accordance with some embodiments of the present invention.

Figure 8:
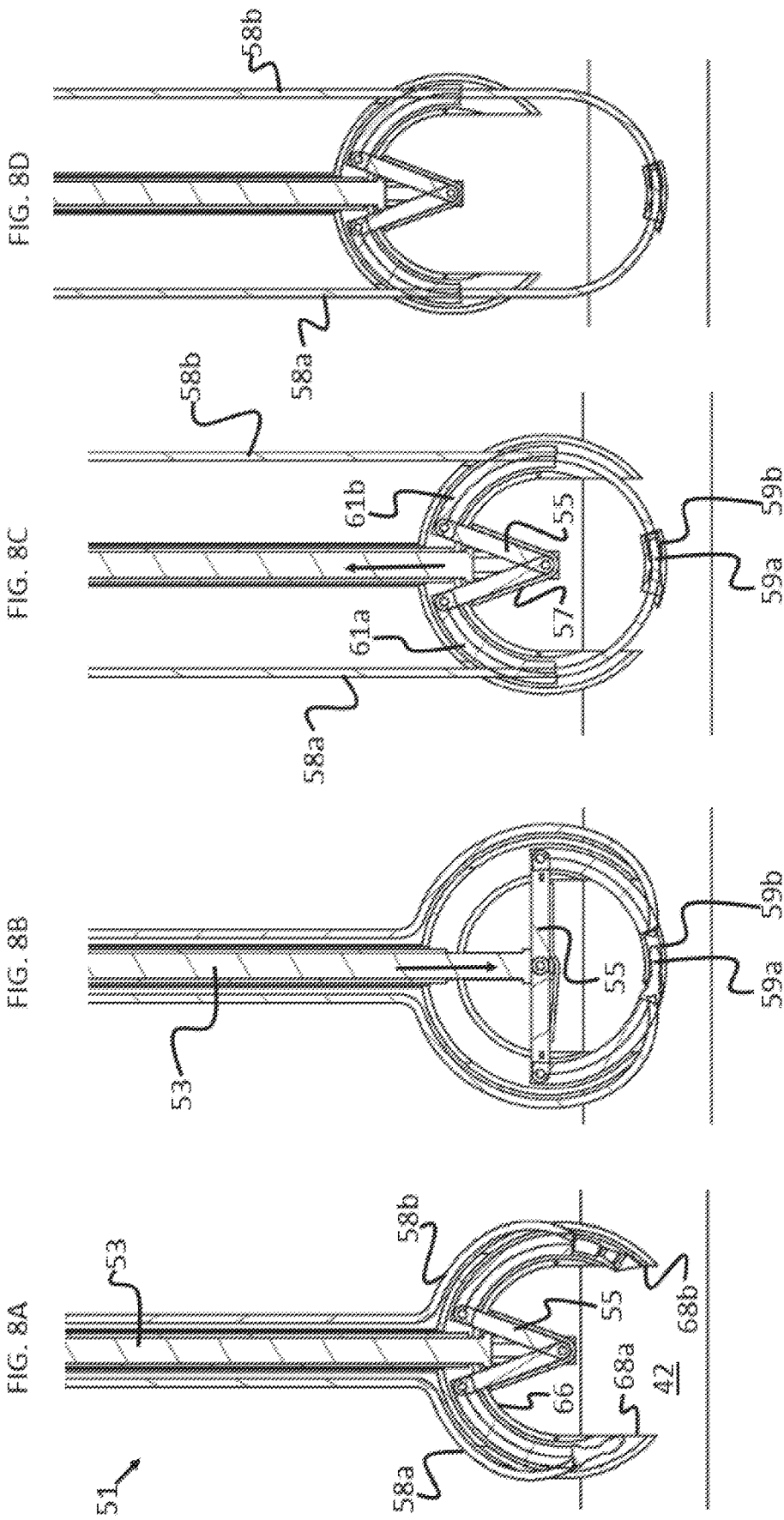
FIGS. 8A-D collectively show the deployment of threads into tissue by a thread-deploying element, in accordance with some embodiments of the present invention.

First, as shown in FIG. 8A, first tube-end 68a and second tube-end 68b penetrate tissue 42. Next, as indicated by the downward-pointing arrow in FIG. 8B, the hinge-control rod is pushed against the hinge, thus causing the hinge to open and passing the arced needles through the tissue. Upon the hinge being sufficiently opened, first pointed distal end 59a couples to second pointed distal end 59b. Subsequently, as indicated by the upward-pointing arrow in FIG. 8C, the hinge-control rod is withdrawn (i.e., moved proximally), such that hinge 55 is closed by spring 57. As the hinge closes, the hinge applies a force to first needle body 61a and second needle body 61b that exceeds the connective force between the needle bodies and the respective distal ends of the needles. Consequently, the needle bodies are detached from the respective distal ends of the needles. Finally, as shown in FIG. 8D, thread-deploying element 51 is withdrawn.

Reference is now made to FIG. 9, which is a schematic illustration of a delivery of an implant 71 to a mitral-valve annulus 75, in accordance with some embodiments of the present invention.

Following the deployment of threads 58, the thread-deployment apparatus is crimped, inserted into catheter 28 and/or sheath 26 (FIG. 1), and then withdrawn from the subject. Subsequently, an implant 71 may be delivered to mitral-valve annulus 75 over the threads. As shown in FIG. 9, implant 71 may comprise an annuloplasty ring. Alternatively, for example, the implant may comprise a replacement valve.

First, implant 71 is loaded onto the threads, by passing the proximal ends of the threads through respective apertures in the implant. (It is noted the implant may be loaded onto the threads even before the threads are deployed.) A single thread that loops through the tissue, as described above for apparatus 20a (FIG. 4), may function as two separate threads, in that each segment (or "arm") of the loop may pass through a different respective aperture in the implant.

Next, a plurality of hollow pushing rods 73, comprising respective distal heads 79, may be loaded onto the threads proximally to the implant. Pushing rods 73 may then push the implant through sheath 26, along the threads, to the valve annulus. It is noted that pushing rods 73 are typically flexible, such that the pushing rods may follow any number of turns within the body of the subject. Similarly, the various other rods, tubes, and other devices used for advancing various elements (e.g., locks) along the threads, as described herein, are typically flexible.

In some embodiments, one or more retraction-threads 69 are looped around implant 71. If the physician ascertains that the implant was improperly positioned (i.e., that the threads were improperly placed), decides to replace implant 71 with another implant (e.g., due to implant 71 being improperly sized or shaped), or decides not to perform any implantation at all, retraction-threads 69 may be used to retract implant 71. Subsequently, even if no implantation is to be performed, there may be no need to operate invasively on the subject; rather, provided that anchors 60 are secure, it may be sufficient to simply cut threads 58.

It is noted that each thread may comprise a polymer, a metal (e.g., Nitinol), and/or any other suitable material. For embodiments in which the threads are metallic, the threads may be alternatively referred to as "wires."

Anchors

Figure 11:
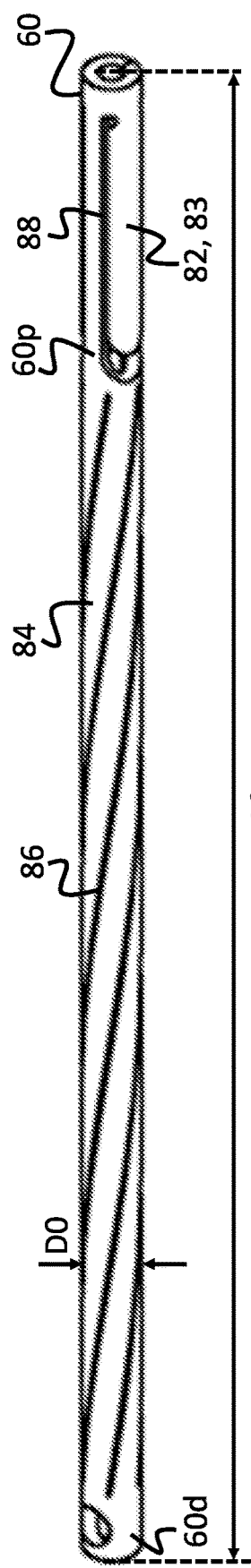
FIG. 11 is a schematic illustration of a tissue anchor in a constrained state, in accordance with some embodiments of the present invention.

Reference is now made to FIG. 10, which is a schematic illustration of tissue anchor 60 held within tube 34, in accordance with some embodiments of the present invention. Reference is additionally made to FIG. 11, which is a schematic illustration of anchor 60 in a constrained state, in accordance with some embodiments of the present invention, to FIG. 11A, which is a schematic illustration of thread 58 attached to the inner wall of the distal portion of tissue anchor 60, in accordance with some embodiments of the present invention, and to FIG. 12, which is a schematic illustration of anchor 60 in an expanded state, in accordance with some embodiments of the present invention. (FIG. 12 shows both an isometric view of the anchor and a view of the anchor from the distal end thereof.)

In some embodiments, anchor 60 comprises a proximal portion 60p, a distal portion 60d, and a plurality of (e.g., between two and eight) strips 84 joining proximal portion 60*p* to distal portion 60*d*. Typically, proximal portion 60*p* is shaped to define one or more (e.g., two) appendages (or "arms") 82, which are joined to the rest of proximal portion 60*p* at the proximal ends thereof. Appendages 82 may comprise, for example, respective prongs 83 or loops.

Figure 11A:
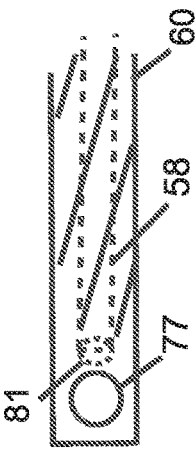
FIG. 11A is a schematic illustration of a thread attached to an inner wall of a distal portion of a tissue anchor, in accordance with some embodiments of the present invention.

Typically, the anchor is at least partly hollow, and the thread passes at least partly through the anchor. To couple the anchor to the thread (i.e., to inhibit the thread from sliding from the anchor), the thread may be knotted distally to the anchor, as shown in FIG. 10. Alternatively, as shown in FIG. 11A, the thread (e.g., the distal end of the thread) may be attached to the inner wall of the distal portion of the anchor, e.g., by the application of an adhesive 81 or by welding. (To facilitate this attachment, distal portion 60*d* may be shaped to define a side opening 77.) As yet another alternative, the thread may be knotted distally to, or attached to the inner wall of, the proximal portion of the anchor. (Typically, polymeric threads are knotted, whereas metallic threads are attached to the inner wall of the anchor.)

In some embodiments, anchor-pushing element 62 comprises a hollow shaft, and thread 58 runs through the shaft. In other embodiments, the anchor-pushing element comprises a solid shaft, and the thread runs through the tube alongside the shaft.

While held within tube 34, anchor 60 is in a constrained state, as shown in FIGS. 10-11, by virtue of the radially-constraining force applied to the anchor by the tube. Typically, while the anchor is constrained, the diameter D0 of the anchor is between 0.3 mm and 2 mm. Alternatively or additionally, the length L0 of the anchor may be between 5 mm and 50 mm.

Typically, the proximal portion of the anchor is shaped to define appendages 82 by virtue of being shaped to define respective grooves 88 beneath the appendages; in other words, typically, appendages 82 are cut out from the proximal portion of the anchor. Thus, advantageously, while constrained, the appendages may not extend radially more than does any other portion of the anchor.

Upon tube 34 reaching the site at which thread 58 is to be deployed, the tube is passed through the tissue, and anchor-pushing element 62 is then used to push anchor 60 from the tube. Upon the removal of the radially-constraining force applied by the tube, the anchor expands radially, adopting the expanded state shown in FIG. 12. In particular, strips 84 expand radially to form respective loops, which are typically arranged in a circular formation. In addition, appendages 82 expand radially. Typically, following the expansion of appendages 82, the angle ⊖ between each of the appendages and the longitudinal axis 90 of the proximal portion of the anchor is between 5 and 60 degrees.

Typically, the strips are not parallel to longitudinal axis 90, even while the anchor is constrained. Rather, there is a circumferential angular displacement between the proximal end of each strip, which is connected to proximal portion 60*p*, and the distal end of the strip, which is connected to distal portion 60*d*. For example, as shown for a particular strip 84*a* identified in FIG. 12, the circumferential angle α between the proximal and distal ends of the strip may be at least 5 degrees, e.g., 5-200 degrees, such as 10-30 degrees. Advantageously, by virtue of this angular displacement, the plane 85 defined by each strip following the expansion of the strip is at least partly perpendicular to longitudinal axis 90, and hence, at least partly parallel to surface 92 of the tissue (FIG. 13). Thus, the strips may distribute the stress applied to the tissue over a larger area.

Typically, anchor 60 is manufactured from a tube of a shape-memory material, such as Nitinol. Strips 84 are formed by cutting slits 86 (e.g., helical slits) in the middle portion of the tube, while appendages 82 are formed by cutting grooves 88 in the proximal portion of the tube. (Slits 86 and grooves 88 may be laser-cut, or may be formed using any other suitable technique.) Following the cutting of slits 86 and grooves 88, the anchor is heat-set in its expanded shape.

Reference is row made to FIG. 13, which is a schematic illustration of anchor 60 anchoring thread 58 at tissue 42, in accordance with some embodiments of the present invention.

To anchor thread 58, tube 34 (FIG. 10) is passed through tissue 42. Subsequently, anchor 60 is partly pushed from the tube, such that strips 84 expand radially at the distal side (or "far side") of tissue 42, i.e., the side of the tissue that is opposite the proximal side (or "near side") at which implant 71 is to be implanted. By virtue of the expansion of the strips (which, in their expanded state, may alternatively be referred to as "loops"), the anchor and thread are inhibited from migrating proximally from the tissue.

Next, the thread is pulled such that strips 84 are pulled against the distal surface 92 of the tissue. While the thread is pulled, the tube is withdrawn from over the proximal portion of the anchor, such that appendages 82 also expand. Depending on the distance between the appendages and the strips relative to the thickness of the tissue, the appendages may expand within the tissue (as in FIG. 13) or at the proximal side of the tissue, e.g., such that the distal ends of the appendages contact the proximal surface 94 of the tissue. In either case, by virtue of the expanded appendages engaging with tissue, the anchor and thread are inhibited from migrating distally from the tissue.

Typically, following the expansion of the strips, the diameter D1 of the strips, which may also be referred to as the maximum diameter of the anchor, is between 4 and 30 mm. Alternatively or additionally, the length L1 of the anchor—which, due to the radial expansion of the strips, is less than length L0 (FIG. 11)—may be between 4 and 30 mm.

Following the expansion of all the anchors, the tubes are withdrawn from the subject. Subsequently, implant 71 is delivered over the threads, as described above with reference to FIG. 9. Next, following the withdrawal of pushing rods 73 (FIG. 9), respective locks 80 (illustrated schematically in FIG. 13, without structural details) are advanced, over the threads, to the implant. As described in detail below with reference to the subsequent figures, which show various embodiments of locks 80, the locks grip the threads proximally to the implant, thus locking the implant over the threads.

Locks

Each of the various locks described hereinbelow comprises a lock body configured to advance to the implant over one of the threads, the lock body comprising at least one rotatable element. The lock body is configured to grip the thread proximally to the implant upon rotation of the rotatable element. Each of the locks further comprises a rotation-maintaining element, configured to inhibit a reversal of the rotation of the rotatable element—i.e., configured to maintain the rotatable element in its rotated position, and hence maintain the gripping of the thread—by engaging with the lock body.

For further details, reference is first made to FIG. 14, which is a schematic illustration of a lock 80*a*, in accordance with some embodiments of the present invention. Reference is further made to FIGS. 15A-B, which are schematic illustrations of longitudinal cross-sections through lock 80*a*, in accordance with different respective embodiments of the present invention.

Lock 80*a* comprises a lock body 96, comprising a pin 100, which may alternatively be referred to as a "wire" or "rod," and a rotatable element 102 rotatably coupled to pin 100 by virtue of the pin passing through rotatable element 102. (Rotatable element 102, along with each of the other rotatable elements described herein, may have any suitable shape.) Typically, the lock body further comprises two support blocks 106, one on each side of element 102, which support the pin; in other words, typically, the pin passes through element 102 from one support block 106 to the other support block. Rotatable element 102 is configured to lock the implant over thread 58 by rotating towards another portion of lock body 96, such that the rotatable element presses the thread against the other portion of the lock body.

For example, the lock body may comprise a block 104, which does not rotate, and the rotatable element may press the thread against block 104 upon the rotation of the rotatable element towards the block. (Block 104, along with each of the other blocks described herein, may have any suitable shape.) Alternatively, instead of block 104, the lock body may comprise another, opposing rotatable element, and the pair of opposing rotatable elements may be configured to rotate towards one another, thus gripping the thread between them.

Lock 80*a* further comprises a ring 98, configured to cause the rotatable element to rotate, and to inhibit a reversal of the rotation, by fitting over the rotatable element. (As shown in FIG. 14, the ring may fit over the rotatable element by virtue of fitting over the entire lock body.) In some embodiments, block 104 is shaped to define one or more notches 108, and ring 98 is shaped to define respective tabs 110 configured to fit into notches 108. Advantageously, the fitting of tabs 110 into the notches inhibits the ring from sliding off the lock body.

In some embodiments, as shown in FIG. 15A, the rotatable element and/or block 104 comprises a jagged surface 116, and the lock body is configured to grip the thread with jagged surface 116. Alternatively or additionally, as shown in FIG. 15B, block 104 may be shaped to define a depression 114, rotatable element 102 may be shaped to define a complementary protrusion 112 configured to fit into depression 114 upon the rotation of the rotatable element, and the lock body may be configured to grip the thread between protrusion 112 and the depression 114. Advantageously, the jagged surface, and/or the curvature in the portion of the thread that is pressed by the protrusion into the depression, increases the friction that would be generated by any sliding of the thread through the lock body, thus inhibiting any such sliding.

Reference is now made to FIG. 16A, which is a schematic illustration of a locking device 118*a* for locking lock 80*a* over the implant, in accordance with some embodiments of the present invention. Reference is further made to FIG. 16B, which is a schematic illustration of a longitudinal cross-section through part of device 118*a*, in accordance with some embodiments of the present invention.

Device 118*a* comprises an outer longitudinal element 120, configured to lock 80*a* by pushing ring 98 onto rotatable element 102. Typically, outer longitudinal element 120 comprises a distal tube 120*d*, or any other suitably-shaped structure, having an inner diameter and/or an outer diameter that is the same as that of the ring, such that the distal surface of tube 120*d* may contact the proximal surface of the ring. Typically, the outer longitudinal element further comprises a narrower, more proximal tube 120*p*, which is joined to distal tube 120*d*.

Typically, device 118*a* further comprises an inner longitudinal element 122, configured to advance lock body 96 over the thread while the thread passes through inner longitudinal element 122 and the inner longitudinal element passes through the outer longitudinal element.

For further details, reference is now additionally made to FIG. 17, which is a schematic illustration of the advancing of the lock body over the thread, in accordance with some embodiments of the present invention, and to FIG. 18, which is a schematic illustration of the pushing of the ring onto the lock body, in accordance with some embodiments of the present invention.

Typically, the ring and lock body are advanced together over the thread. For example, the ring may be partly loaded onto lock body 96, such that the ring covers the proximal portion of the lock body, at which pin 100 is disposed, without pushing the distal portion of the rotatable element against the thread. Subsequently, the outer longitudinal element and inner longitudinal element may be advanced over the thread, which passes between rotatable element 102 and block 104, such that both the ring and the lock body are advanced from the exterior of the subject to the implant. (By virtue of the ring being partly loaded onto the lock body, the outer longitudinal element may advance the lock body by virtue of pushing the ring, and/or the inner longitudinal element may advance the ring by virtue of pushing the lock body.) Subsequently, in response to the lock contacting the implant, the outer longitudinal element may be used to push the ring further over the lock body while the implant provides a counterforce to the lock body, thus forcing the rotation of the rotatable element.

In some embodiments, inner longitudinal element 122 is shaped to define an aperture 124 (or a notch), and one of tabs 110 is configured to fit into aperture 124 while the lock body is advanced over the thread. Advantageously, aperture 124 facilitates advancing the ring and the lock body together, by inhibiting the ring from sliding off the lock body.

For example, the ring may be loaded onto the lock body such that a proximal tab 110*p* of the ring fits into aperture 124, and a distal tab 110*d* of the ring fits into one of notches 108, such as the most proximal notch 108. Subsequently, the pushing force applied to the ring by the outer longitudinal element may force proximal tab 110*p* out of aperture 124, and then push the ring over the lock body until proximal tab 110*p* snaps into one of notches 108, such as the most proximal notch 108.

Typically, in such embodiments, the inner longitudinal element comprises a distal tube 122*d*, or any other suitably-shaped structure, which has an outer diameter that is the same as the inner diameter of ring 98 and is shaped to define aperture 124, such that tab 110*p* may fit into the aperture. Typically, the inner longitudinal element further comprises a narrower proximal tube 122*p*, which is joined to distal tube 122*d*.

Typically, inner longitudinal element 122 comprises a sharp distal edge 126 configured to cut thread 58 subsequently to the pushing of the ring onto rotatable element 102. For example, following the locking of the lock, device 118*a* may be withdrawn slightly from the lock. Subsequently, the inner longitudinal element may be pushed out of the outer longitudinal element, such that edge 126 cuts the thread. Subsequently, device 118*a* and the proximal portion of thread 58 may be removed from the subject.

Reference is now made to FIG. 19, which is a schematic illustration of another lock 80b, in accordance with some embodiments of the present invention.

Lock 80b is similar to lock 80a (FIG. 14) in several ways. For example, lock 80b also comprises lock body 96, comprising at least one rotatable element. As a specific example, lock 80b may comprise a block 103, a first rotatable element 102a disposed at one side of block 103, and a second rotatable element 102b disposed at the opposite side of the block, pin 100 passing through the block and the two rotatable elements. Furthermore, similarly to lock 80a, lock 80b comprises ring 98, which is configured to cause the rotatable element(s) to rotate by fitting over the lock body.

However, lock 80b also differs from lock 80a. For example, in lock 80b, the lock body comprises a shaft 130 disposed next to the at least one rotatable element (e.g., between first rotatable element 102a and second rotatable element 102b, opposite block 103), and ring 98 is configured to cause the rotatable element to rotate by fitting over shaft 130 such that the ring pushes the rotatable element(s). Moreover, the lock body comprises another pin 128. Further details regarding these features, along with other features of lock 80b, are described below with reference to the subsequent figures.

Reference is now made to FIG. 20A, which is a schematic illustration of a locking device 118b for locking lock 80b over the implant, in accordance with some embodiments of the present invention. Reference is also made to FIG. 20B, which is a schematic illustration of a longitudinal cross-section through part of device 118b, in accordance with some embodiments of the present invention. (For clarity, rotatable element 102a is drawn transparently in FIG. 20B.)

Device 118b comprises a hollow inner longitudinal element 132, configured to push the ring onto shaft 130. For example, inner longitudinal element 132 may comprise an inner tube 138 and a ring-pushing appendage 140, which is shaped to define a side opening 142, coupled to and extending beyond the distal end of inner tube 138. In such embodiments, the inner longitudinal element may push the ring onto the shaft while ring-pushing appendage 140 contacts the ring and the thread passes through the inner tube via side opening 142. (In some embodiments, the ring-pushing appendage comprises a ring having multiple distally-protruding legs 144, between which side opening 142 is disposed.) Alternatively, inner tube 138 itself may be shaped to define side opening 142, such that the inner tube may push the ring onto the shaft while the inner tube contacts the ring and the thread passes through the side opening.

Device 118b further comprises a hollow outer longitudinal element 134, configured to advance the lock body over thread 58 while the thread passes through the inner longitudinal element (as described above) and the inner longitudinal element passes through outer longitudinal element 134. For example, outer longitudinal element 134 may comprise an outer tube 136 that contacts the lock body, such that outer tube 136 pushes the lock body directly. Alternatively, the outer longitudinal element may comprise, in addition to outer tube 136, an appendage 146—comprising another tube, for example, that is wider than outer tube 136—coupled to and extending from the distal end of the outer tube, such that the outer longitudinal element pushes the lock body by virtue of appendage 146 contacting the lock body.

Typically, outer longitudinal element 134 is configured to hold the lock body while advancing the lock body over the thread. For example, appendage 146 (or the outer tube itself) may be shaped to define an aperture 148, block 103 may be shaped to define a protrusion 150, and the outer longitudinal element may hold the lock body by virtue of protrusion 150 passing through aperture 148.

Figure 22:
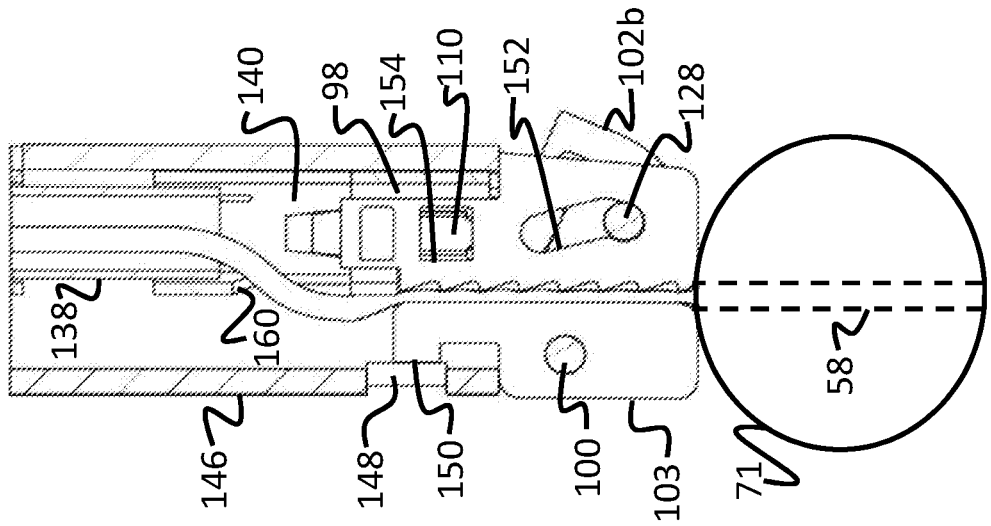
FIG. 22 is a schematic illustration of a pushing of a ring onto a lock body, in accordance with some embodiments of the present invention.
Figure 21:
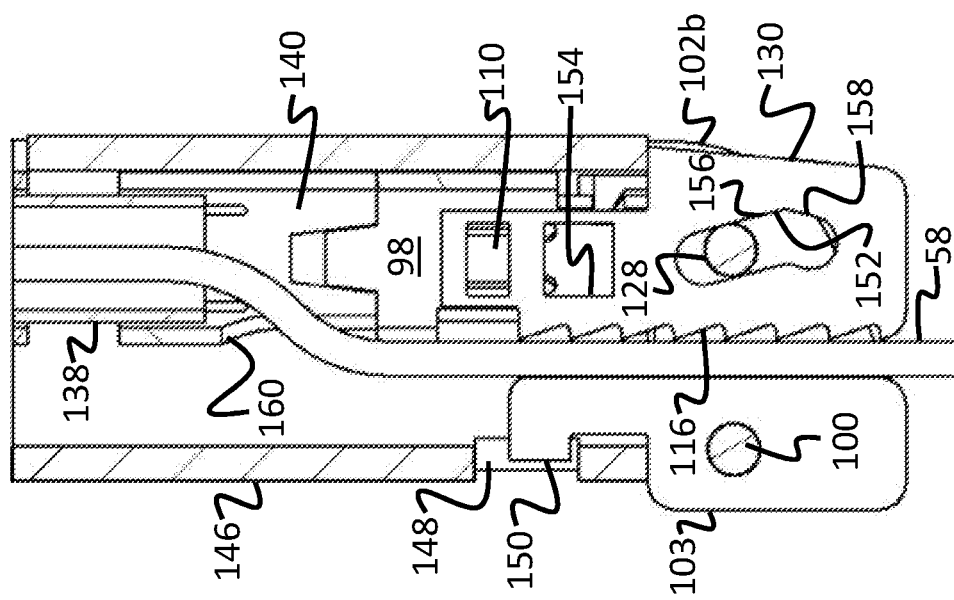
FIG. 21 is a schematic illustration of an advancing of a lock body over a thread, in accordance with some embodiments of the present invention.

Reference is now made to FIG. 21, which is a schematic illustration of the advancing of the lock body over the thread, in accordance with some embodiments of the present invention, and to FIG. 22, which is a schematic illustration of the pushing of the ring onto the lock body, in accordance with some embodiments of the present invention. (FIGS. 21-22 show a longitudinal cross-section through device 118b and lock body 96, in which rotatable element 102a is not shown.)

Shaft 130 is shaped to define a slanted slot 152, which, along at least a proximal portion 156 thereof, slants away from block 103. Pin 128, which is coupled to rotatable elements 102a and 102b, passes through slot 152. As described above with reference to FIG. 19, pin 100, which defines the axis of rotation for the rotatable elements, passes through block 103 and the two rotatable elements. Typically, shaft 130 is shaped to define an aperture 154 (or a notch), and tab 110 is configured to fit into aperture 154. In some embodiments, shaft 130 and/or block 103 comprise a jagged surface 116; alternatively or additionally, the shaft and block may be shaped to define a complementary protrusion and depression.

Typically, the lock body and ring 98 are advanced together over thread 58. First, ring 98 is partly loaded onto shaft 130, such that tab 110 is proximal to aperture 154. Subsequently, inner longitudinal element 132 and outer longitudinal element 134 push the lock over thread 58, which passes between block 103 and shaft 130, until the lock contacts implant 71. (By virtue of the ring being partly loaded onto the shaft, the outer longitudinal element may advance the ring by virtue of pushing the lock body, and/or the inner longitudinal element may advance the lock body by virtue of pushing the ring.) While the lock is advanced to the implant, the rotatable elements are in their resting (unrotated) positions, such that pin 128 is disposed at or near the proximal end of slot 152.

In response to the lock contacting the implant, inner longitudinal element 132 is used to push ring 98 further onto the shaft, while the implant provides a counterforce to the pushing. As this pushing is performed, the ring pushes against the rotatable elements, thus causing the rotatable elements to rotate. By virtue of the motion of pin 128 being constrained by slot 152 (and by virtue the distance between the two pins being fixed), the ring, by causing the rotatable elements to rotate, causes block 103 to be pulled toward the shaft, such that the lock body grips the thread between the block and the shaft. Additionally, the rotatable elements, by pulling the block, may pull protrusion 150 from aperture 148, such that the lock body is released from the outer longitudinal element.

Upon tab 110 snapping into aperture 154, the ring is locked over the shaft, thus maintaining the rotated position of the rotatable elements, and hence, the gripping of the thread. To further facilitate the locking of the lock, a distal portion 158 of the slot may slant toward the block, such that pin 128 is inhibited from moving proximally through the slot.

Subsequently to the locking of the lock, the outer longitudinal element and inner longitudinal element are withdrawn. Typically, inner tube 138 or ring-pushing appendage 140 comprises a sharp edge 160 configured to cut the thread subsequently to the pushing of the ring onto the shaft. Hence, the thread may be cut by pushing the inner tube while pulling the thread taut.

It is noted that the above description of FIGS. 21-22 also applies to embodiments in which the lock body comprises a single rotatable element (represented by rotatable element 102b in FIGS. 21-22), rather than two rotatable elements.

Figure 23:
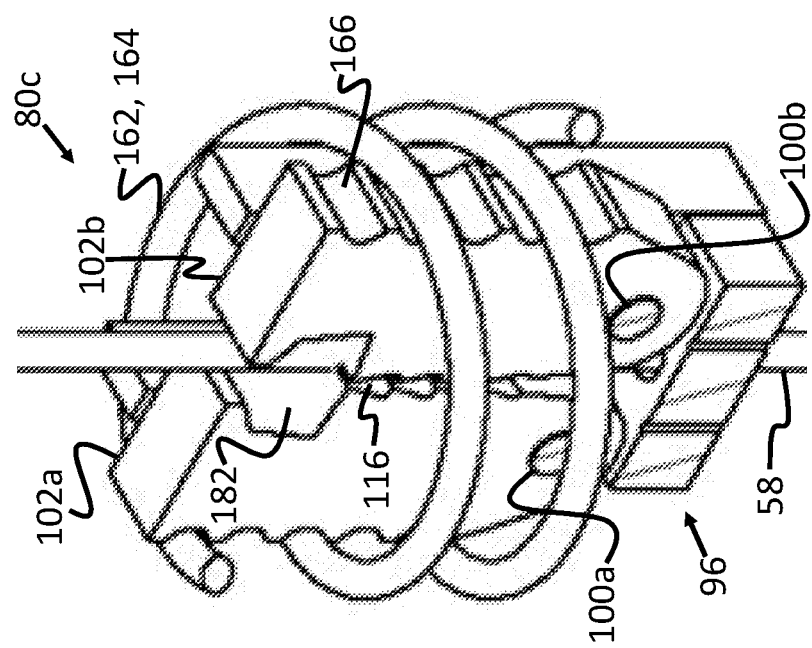
FIG. 23 is a schematic illustration of a lock, in accordance with some embodiments of the present invention.

Reference is now made to FIG. 23, which is a schematic illustration of another lock 80c, in accordance with some embodiments of the present invention.

Similarly to locks 80a and 80b, lock 80c comprises a lock body 96, comprising at least one rotatable element. Furthermore, as in locks 80a and 80b, the lock body is configured to grip thread 58 proximally to the implant upon rotation of the rotatable element.

For example, the lock body may comprise a pair of opposing rotatable elements, which are configured to grip the thread between respective proximal ends of the rotatable elements upon the rotation of the rotatable elements. The pair may comprise a first rotatable element 102a, configured to rotate with respect to a first pin 100a, and a second rotatable element 102b, configured to rotate with respect to a second pin 100b. One or both of the rotatable elements may comprise a jagged surface 116, such that the rotatable elements are configured to grip the thread with the jagged surface; alternatively or additionally, the pair may be shaped to define a complementary protrusion and depression.

Lock 80c differs from locks 80a and 80b, however, at least in that in lock 80c, the rotation-maintaining element comprises a spring 162, comprising a coil 164 coiled around the rotatable elements. Coil 164 is configured to cause the rotatable elements to rotate, and to inhibit any reversal of the rotation, by pushing the rotatable elements together. In some embodiments, to inhibit the coil from sliding off the rotatable elements, at least one of the rotatable elements is shaped to define a ridged surface 166, and coil 164 passes between the ridges of the ridged surface. Further details regarding the locking of lock 80c are described below with reference to the subsequent figures.

Figure 24:
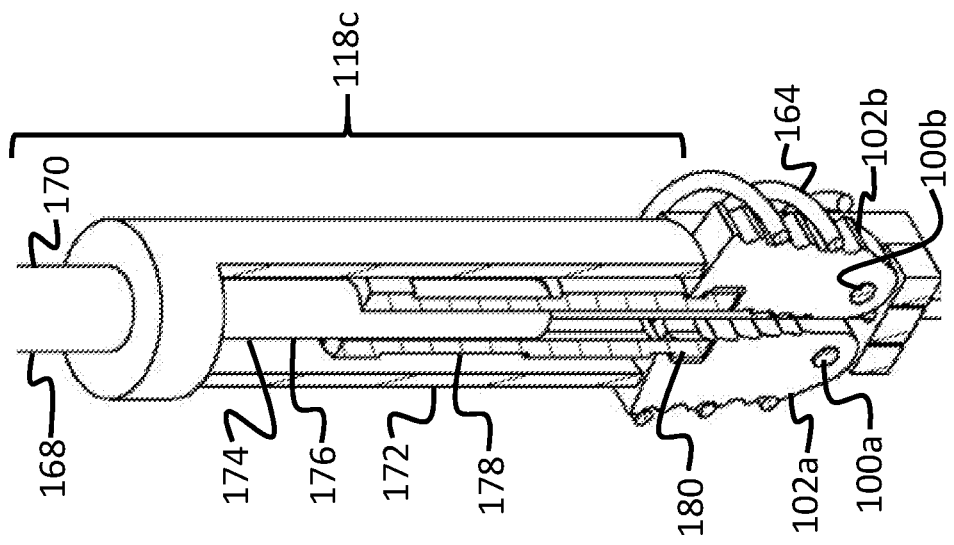
FIG. 24 is a schematic illustration of a locking device for locking a lock over an implant, in accordance with some embodiments of the present invention.

Reference is now made to FIG. 24, which is a schematic illustration of a locking device 118c for locking lock 80c over the implant, in accordance with some embodiments of the present invention. (For clarity, a portion of device 118c is shown inn cross-section.) Reference is further made to FIG. 25, which is a schematic illustration of the advancing of the lock over the thread, in accordance with some embodiments of the present invention, and to FIG. 26, which is a schematic illustration of the locking of the lock, in accordance with some embodiments of the present invention.

Device 118c comprises a hollow outer longitudinal element 168, which may comprise a narrower proximal outer tube 170 joined to a wider distal outer tube 172, and a hollow inner longitudinal element 174. Inner longitudinal element 174 comprises a distal end 180 configured to interpose between the respective proximal ends of the rotatable elements while the lock body is advanced to the implant. By virtue of this interposition, the thread may pass between the rotatable elements (and through the inner longitudinal element) without being gripped by the lock body. In some embodiments, to facilitate this interposition, the respective proximal ends of the rotatable elements are shaped to define respective notches 182, and distal end 180 is configured to fit into notches 182.

In some embodiments, inner longitudinal element 174 comprises an inner tube 176 and an appendage 178, such as a tubular appendage, coupled to and extending from the distal end of tube 176, appendage 178 comprising distal end 180. Alternatively, inner tube 176 itself may comprise distal end 180.

To advance the lock body to the implant, the inner longitudinal element and/or the outer longitudinal element may be used to push the lock body while thread 58 passes through the inner longitudinal element and the inner longitudinal element passes through outer longitudinal element. During the advancement of the lock body, the coil is stretched outward by the rotatable elements by virtue of the interposition of distal end 180.

As shown in FIG. 26, following the advancement of the lock body, in response to the lock body contacting the implant, the distal end of the inner longitudinal element is withdrawn from between the pair of rotatable elements while the outer longitudinal element applies a counterforce to the lock body. The withdrawal of the inner longitudinal element causes the coil to spring inwards from its stretched state, thus pushing the pair of rotatable elements toward one another such that the pair rotate toward one another and hence grip the thread therebetween.

Subsequently to the locking of the lock, device 118c is withdrawn. In some embodiments, the outer longitudinal element comprises a sharp distal edge 184 configured to cut the thread subsequently to the rotation of the rotatable elements.

In some embodiments, the lock body comprises a single rotatable element and an opposing (non-rotatable) block. In such embodiments, the coil is coiled around the rotatable element and the block, such that the coil causes the thread to be gripped between the rotatable element and the block. The rotatable element and/or the block may comprise a jagged surface; alternatively or additionally, these elements may be shaped to define a complementary protrusion and depression.

Reference is now made to FIG. 27, which is a schematic illustration of another lock 80d, in accordance with some embodiments of the present invention.

Similarly to lock 80c, lock 80d comprises a spring 162 configured to maintain the rotated position of rotatable element 102. However, in lock 80d, the rotatable element is shaped to define an aperture 186, and spring 162 comprises a wire 188 configured to spring into aperture 186 following the rotation of the rotatable element, thus inhibiting any reversal of the rotation.

For example, in lock 80d, lock body 96 may comprise a first panel 190a, a second panel 190b, and a block 192 disposed between first panel 190a and second panel 190b. As shown in FIGS. 31-32, which are described below, wire 188 may run along second panel 190b, through second panel 190b, through rotatable element 102, through first panel 190a, and finally, through a groove 194 (or an aperture) inn first panel 190a, such that the end of the wire reaches the rotatable element. Upon the rotation of the rotatable element with respect to wire 188 (i.e., with respect to the axis of rotation defined by the wire), the rotatable element presses the thread against block 192, and wire 188 springs into aperture 186.

For further details, reference is now made to FIG. 28A, which is a schematic illustration of a locking device 118d for locking the lock over the implant, in accordance with some embodiments of the present invention, and to FIG. 28B, which shows a longitudinal cross-section through a portion of device 118d, in accordance with some embodiments of the present invention. (In FIG. 28B, first panel 190a is not shown, such that rotatable element 102 is exposed.) Reference is also made to FIG. 29, which is a schematic illustration of the advancing of the lock over thread 58, in accordance with some embodiments of the present invention, and to FIG. 30, which is a schematic illustration of the locking of the lock, in accordance with some embodiments of the present invention. (The right portion of each of FIGS. 29-30 shows the lock body as viewed from the side of the left portion of the figure, with block 192 hidden to expose rotatable element 102.)

Device 118d comprises an outer longitudinal element 196, comprising, for example, an outer tube. Device 118d further comprises an inner longitudinal element 198, comprising, for example, an inner tube. To advance the lock body to the implant, outer longitudinal element 196 and/or inner longitudinal element 198 may be used to push the lock body while thread 58 passes through the inner longitudinal element and the inner longitudinal element passes through the outer longitudinal element.

Typically, the distal end of the inner longitudinal element is shaped to define an aperture 202 (or a notch), and rotatable element 102 is shaped to define a protrusion 204 configured to fit inside aperture 202. As shown in FIG. 29, while the lock body is advanced to the implant, protrusion 204 is inside aperture 202, and thread 58 runs between the rotatable element and block 192 without being gripped by the lock body. Also, during the advancement of the lock body, wire 188 is deformed from its resting state, in that the end 208 of wire 188 is pushed away from the lock body by rotatable element 102.

As shown in FIG. 30, in response to the lock body contacting the implant, inner longitudinal element 198 is withdrawn from the lock body while outer longitudinal element 196 applies a counterforce to the lock body. The withdrawal of the inner longitudinal element dislodges protrusion 204 from aperture 202 and rotates the rotatable element, such that a surface 206 of the rotatable element presses the thread against block 192. (Surface 206 may be jagged, and/or surface 206 and block 192 may be shaped to define a complementary protrusion and depression.) The rotation of the rotatable element also aligns aperture 186 with end 208 of the wire, such that the wire springs into the aperture and hence locks the rotatable element in its rotated position.

Typically, inner longitudinal element 198 is shaped to define a side opening 200, and the inner longitudinal element is configured to advance the lock body to the implant while the thread passes through the inner longitudinal element via side opening 200. Typically, the outer longitudinal element is also shaped to define a side opening 210, such that the thread passes through the lock body, through side opening 210, through side opening 200, and through the inner longitudinal element. In such embodiments, the inner longitudinal element may comprise a sharp edge 212 at least partly surrounding side opening 200 and configured to cut the thread upon the withdrawal of the inner longitudinal element.

In some embodiments, for cases which an implant requires multiple locks, the locks are delivered to the implant and locked in sequence, e.g., using the same locking device to deliver and lock each of the locks. In other embodiments, the locks are delivered simultaneously, and are locked, using different respective locking devices. For example, multiple locks 80a may be delivered and locked using different respective locking devices 118a. In such embodiments, the locking devices may also be used, instead of pushing rods 73 (FIG. 9), to deliver the implant. That is, the implant may be loaded onto the threads, the locks may be loaded onto the threads proximally to the implant, and the locking devices may then advance the implant, together with the locks, to the implantation site.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus, comprising:
   a thread; and
   a tissue anchor, comprising:
      a proximal portion, shaped to define one or more straight radially-expandable appendages configured to expand radially, without curving, by pivoting with respect to a remainder of the proximal portion;
      a distal portion; and
      a plurality of radially-expandable strips joining the proximal portion to the distal portion,
      the anchor being coupled to the thread so as to render the anchor configured to anchor the thread at tissue of a subject by virtue of the appendages expanding radially within the tissue, and the strips expanding radially to form respective loops at a distal side of the tissue, upon removal of a radially-constraining force from the anchor.

2. The apparatus according to claim 1, wherein the strips are configured to expand such that the loops are arranged in a circular formation.

3. The apparatus according to claim 1, wherein the thread passes at least partly through the anchor.

4. The apparatus according to claim 3, wherein the anchor is coupled to the thread by virtue of the thread being knotted distally to the anchor.

5. The apparatus according to claim 3, wherein the anchor is coupled to the thread by virtue of the thread being attached to an inner wall of the distal portion of the anchor.

6. The apparatus according to claim 1, wherein the strips consist of 2-8 strips.

7. The apparatus according to claim 1, wherein, for each of the strips, a circumferential angle between a proximal end of the strip and a distal end of the strip is at least 5 degrees.

8. The apparatus according to claim 7, wherein the circumferential angle is between 10 and 30 degrees.

9. The apparatus according to claim 1, wherein the proximal portion of the anchor is shaped to define the appendages by virtue of being shaped to define respective grooves beneath the appendages.

10. The apparatus according to claim 9, wherein, prior to the removal of the constraining force, the appendages do not extend radially more than does any other portion of the anchor.

11. The apparatus according to claim 1, wherein, following the expansion of the appendages, an angle between each of the appendages and a longitudinal axis of the proximal portion of the anchor is between 5 and 60 degrees.

12. A method, comprising:
   delivering a tissue anchor, which is radially constrained within a tube and is coupled to a thread, to a proximal side of tissue of a subject;
   piercing the tube through the tissue to a distal side of the tissue; and
   subsequently to piercing the tube through the tissue, anchoring the thread at the tissue, by pushing the anchor from the tube such that one or more appendages at a proximal portion of the anchor expand radially within the tissue, and a plurality of strips, which join the proximal portion of the anchor to a distal portion of the anchor, expand radially to form respective loops at the distal side of the tissue.

13. The method according to claim 12, wherein the thread passes at least partly through the anchor.

14. The method according to claim 13, wherein the anchor is coupled to the thread by virtue of the thread being knotted distally to the anchor.

15. The method according to claim 12, wherein the anchor is coupled to the thread by virtue of the thread being attached to an inner wall of the distal portion of the anchor.

16. The method according to claim 12, wherein the strips consist of 2-8 strips.

17. The method according to claim 12, wherein the proximal portion of the anchor is shaped to define the appendages by virtue of being shaped to define respective grooves beneath the appendages.

18. The method according to claim 12, wherein, while the tissue anchor is radially constrained within the tube, the appendages do not extend radially more than does any other portion of the anchor.

19. The method according to claim 12, wherein, following the expansion of the appendages, an angle between each of the appendages and a longitudinal axis of the proximal portion of the anchor is between 5 and 60 degrees.

* * * * *